(12) United States Patent
Nelsen et al.

(10) Patent No.: US 6,939,397 B2
(45) Date of Patent: Sep. 6, 2005

(54) SYSTEM FOR PURIFYING AND REMOVING CONTAMINANTS FROM GASEOUS FLUIDS

(75) Inventors: Roger Nelsen, Tolland, CT (US); John Longan, Burlington, VT (US); Guan Fumin, Shanghai (CN)

(73) Assignee: Eco-Rx, Inc., Brewster, MA (US)

( * ) Notice: Subject to any disclaimer, the term of this patent is extended or adjusted under 35 U.S.C. 154(b) by 0 days.

(21) Appl. No.: 10/841,831

(22) Filed: May 10, 2004

(65) Prior Publication Data

US 2005/0000365 A1 Jan. 6, 2005

Related U.S. Application Data

(60) Provisional application No. 60/468,655, filed on May 8, 2003.

(51) Int. Cl.[7] .............................................. B01D 50/00
(52) U.S. Cl. .......................... 96/224; 55/418; 422/124; 95/273
(58) Field of Search ............................ 96/224; 95/273; 422/124; 55/418

(56) References Cited

U.S. PATENT DOCUMENTS

| | | | |
|---|---|---|---|
| 1,594,635 A | 8/1926 | Skogland | |
| 1,773,220 A | 8/1930 | Credicott | |
| 1,966,059 A | 7/1934 | Chiera | |
| 1,969,765 A | 8/1934 | Spanner et al. | |
| 2,042,162 A | 5/1936 | Schouwstra | |
| 2,043,925 A | 6/1936 | Epstein | |
| 2,150,263 A | 3/1939 | Chesney | |
| 2,173,073 A | 9/1939 | Pierson | |
| 2,183,387 A | 12/1939 | Anderson | |
| 2,220,895 A | 11/1940 | Epstein | |
| 2,248,713 A | 7/1941 | Locke | |
| 2,290,376 A | 7/1942 | Marshall | |
| 2,362,384 A | 11/1944 | Libby | |
| 2,362,385 A | 11/1944 | Libby | |
| 2,628,083 A | 2/1953 | Rense | |
| 3,001,230 A | 9/1961 | Rossi | |

(Continued)

FOREIGN PATENT DOCUMENTS

| | | |
|---|---|---|
| DE | 3837905 | 5/1990 |
| GB | 2036951 A | 7/1980 |
| GB | 2212370 A | 7/1989 |
| JP | 77/66872 | 6/1977 |
| JP | 1-224030 | 9/1989 |
| WO | WO 90/05909 | 5/1990 |
| WO | WO 97/22794 | 6/1997 |
| WO | WO 97/34682 | 9/1997 |
| WO | WO 98/41315 | 9/1998 |
| WO | WO 99/13922 | 3/1999 |
| WO | WO 99/13956 | 3/1999 |
| WO | WO 99/22777 | 5/1999 |
| WO | WO 99/26668 | 6/1999 |
| WO | WO 00/06209 | 2/2000 |

*Primary Examiner*—Robert A. Hopkins
(74) *Attorney, Agent, or Firm*—Edell, Shapiro & Finnan, LLC

(57) ABSTRACT

A system and corresponding methods for purifying and removing contaminants from gaseous fluids includes a housing including an inlet, an outlet, and an elongated UV chamber disposed within the housing. The UV radiation source is disposed longitudinally within the UV chamber. At least one baffle structure is disposed at an upstream location within the housing to restrict flow as well as to generate a turbulent flow of the gaseous fluid within the UV chamber. In addition, a fan is disposed at a selected location within the housing to facilitate a flow of the gaseous fluid through the housing at a selected flow rate. The dimensions of the UV chamber and UV source and the configuration of the baffle structure are selected to increase the exposure time and mixing of fluid flowing through the UV chamber as well as increase the proximity of the flowing fluid to the UV source.

43 Claims, 9 Drawing Sheets

U.S. PATENT DOCUMENTS

| | | |
|---|---|---|
| 3,011,230 A | 12/1961 | Potapenko |
| 3,071,828 A | 1/1963 | Cornell, Jr. |
| 3,198,214 A | 8/1965 | Lorenz |
| 3,252,036 A | 5/1966 | Elmer et al. |
| 3,258,631 A | 6/1966 | Elmer et al. |
| 3,294,480 A | 12/1966 | Potapenko |
| 3,374,381 A | 3/1968 | Albinak et al. |
| 3,486,308 A | 12/1969 | Burt |
| 3,558,958 A | 1/1971 | Tarktakoff et al. |
| 3,576,593 A | 4/1971 | Circirello |
| 3,670,193 A | 6/1972 | Thorington et al. |
| 3,674,421 A | 7/1972 | Decupper |
| 3,731,699 A | 5/1973 | Hallum |
| 3,744,216 A | 7/1973 | Halloran |
| 3,750,556 A | 8/1973 | Duke et al. |
| 3,780,767 A | 12/1973 | Borg et al. |
| 3,785,124 A | 1/1974 | Gaylord |
| 3,788,041 A | 1/1974 | Gaylord |
| 3,790,801 A | 2/1974 | Coleman |
| 3,798,922 A | 3/1974 | Duke et al. |
| 3,802,158 A | 4/1974 | Ohle |
| 3,818,678 A | 6/1974 | Gothard |
| 3,835,626 A | 9/1974 | Miyake et al. |
| 3,844,741 A | 10/1974 | Dimitrik |
| 3,872,349 A | 3/1975 | Spero et al. |
| 3,894,236 A | 7/1975 | Hazelrigg |
| 3,905,920 A | 9/1975 | Botcharoff |
| 3,937,967 A | 2/1976 | Steinitz |
| 3,954,407 A | 5/1976 | Andary et al. |
| 3,976,448 A | 8/1976 | Eng et al. |
| 4,019,986 A | 4/1977 | Burris et al. |
| 4,033,719 A | 7/1977 | Conn et al. |
| 4,042,850 A | 8/1977 | Ury et al. |
| 4,074,165 A | 2/1978 | Moriyama |
| 4,118,191 A | 10/1978 | Bohnensieker |
| 4,156,652 A | 5/1979 | Wiest |
| 4,163,650 A | 8/1979 | Watson et al. |
| 4,179,616 A | 12/1979 | Coviello et al. |
| 4,184,076 A | 1/1980 | Kosnoff |
| 4,189,363 A | 2/1980 | Beitzel |
| 4,203,948 A | 5/1980 | Brundbjerg |
| 4,210,429 A | 7/1980 | Golstein |
| 4,233,323 A | 11/1980 | Sway et al. |
| 4,244,710 A | 1/1981 | Burger |
| 4,253,852 A | 3/1981 | Adams |
| 4,273,660 A | 6/1981 | Beitzel |
| 4,276,943 A | 7/1981 | Holmes |
| 4,309,388 A | 1/1982 | Tenney et al. |
| 4,330,403 A | 5/1982 | Fuchs |
| 4,336,480 A | 6/1982 | Kobayashi |
| 4,359,668 A | 11/1982 | Ury |
| 4,366,525 A | 12/1982 | Baumgartner |
| 4,382,866 A | 5/1983 | Johnson |
| 4,422,450 A | 12/1983 | Rusteberg |
| 4,468,372 A | 8/1984 | Seifert, deceased et al. |
| 4,484,517 A | 11/1984 | Amann |
| 4,491,551 A | 1/1985 | Johnson |
| 4,496,375 A | 1/1985 | Le Vantine |
| 4,504,445 A | 3/1985 | Walz |
| 4,535,247 A | 8/1985 | Kurtz |
| 4,541,847 A | 9/1985 | Oie et al. |
| 4,549,477 A | 10/1985 | McCabe, Jr. |
| 4,553,992 A | 11/1985 | Boissinot et al. |
| 4,562,014 A | 12/1985 | Johnson |
| 4,563,286 A | 1/1986 | Johnson et al. |
| 4,597,781 A | 7/1986 | Spector |
| 4,621,195 A | 11/1986 | Larsson |
| 4,640,782 A | 2/1987 | Burleson |
| 4,655,933 A | 4/1987 | Johnson et al. |
| 4,658,707 A | 4/1987 | Hawkins et al. |
| 4,665,707 A | 5/1987 | Hamilton |
| 4,760,264 A | 7/1988 | Barrett |
| 4,780,277 A | 10/1988 | Tanaka et al. |
| 4,782,552 A | 11/1988 | Bartlett et al. |
| 4,783,878 A | 11/1988 | McCambridge |
| 4,806,768 A * | 2/1989 | Keutenedjian |
| 4,806,770 A | 2/1989 | Hylton et al. |
| 4,819,276 A | 4/1989 | Stevens |
| 4,849,115 A | 7/1989 | Cole et al. |
| 4,849,862 A | 7/1989 | Diskin et al. |
| 4,861,356 A | 8/1989 | Penney |
| 4,861,484 A | 8/1989 | Lichtin et al. |
| 4,863,687 A | 9/1989 | Stevens et al. |
| 4,863,748 A | 9/1989 | Herschler |
| 4,865,749 A | 9/1989 | Yoshida |
| 4,892,712 A | 1/1990 | Robertson et al. |
| 4,898,679 A | 2/1990 | Siegel et al. |
| 4,900,344 A | 2/1990 | Lansing |
| 4,904,289 A | 2/1990 | Miyakami et al. |
| 4,904,422 A | 2/1990 | Silverman |
| 4,913,827 A | 4/1990 | Nebel |
| 4,954,465 A | 9/1990 | Kawashima et al. |
| 4,954,755 A | 9/1990 | Lynch et al. |
| 4,966,759 A * | 10/1990 | Robertson et al. |
| 4,983,307 A * | 1/1991 | Nesathurai |
| 4,990,311 A * | 2/1991 | Hirai et al. |
| 4,992,169 A * | 2/1991 | Izumiya |
| 4,999,201 A * | 3/1991 | Okamoto et al. |
| 5,006,758 A * | 4/1991 | Gellert et al. |
| 5,008,550 A * | 4/1991 | Barrett |
| 5,015,394 A * | 5/1991 | McElhenney et al. |
| 5,015,442 A * | 5/1991 | Hirai |
| 5,019,256 A * | 5/1991 | Ifill et al. |
| 5,029,252 A * | 7/1991 | Ameseder |
| 5,032,291 A * | 7/1991 | Sublette |
| 5,035,728 A * | 7/1991 | Fang |
| 5,037,583 A * | 8/1991 | Hand |
| 5,039,918 A * | 8/1991 | Ohtake et al. |
| 5,055,115 A | 10/1991 | Yikai et al. |
| 5,069,880 A | 12/1991 | Karlson |
| 5,078,971 A | 1/1992 | Matuda et al. |
| 5,087,428 A | 2/1992 | Fletcher et al. |
| 5,107,687 A * | 4/1992 | Candeloro |
| 5,110,511 A | 5/1992 | Hand |
| 5,114,372 A | 5/1992 | Fuchs |
| 5,126,111 A | 6/1992 | Al-Ekabi et al. |
| 5,133,788 A | 7/1992 | Backus |
| 5,133,904 A | 7/1992 | Pepper |
| 5,157,758 A | 10/1992 | Halberstadt et al. |
| 5,166,527 A | 11/1992 | Solymar |
| 5,166,528 A | 11/1992 | Le Vay |
| 5,186,903 A | 2/1993 | Cornwell |
| 5,213,759 A | 5/1993 | Castberg et al. |
| 5,219,534 A | 6/1993 | Reynolds |
| 5,221,520 A | 6/1993 | Cornwell |
| 5,223,105 A | 6/1993 | Arthurson |
| 5,227,184 A | 7/1993 | Hurst |
| 5,227,698 A | 7/1993 | Simpson et al. |
| 5,230,220 A * | 7/1993 | Kang et al. |
| 5,230,792 A | 7/1993 | Sauska et al. |
| 5,248,323 A | 9/1993 | Stevenson |
| 5,250,232 A | 10/1993 | Pepper et al. |
| 5,250,258 A | 10/1993 | Oh |
| 5,268,009 A | 12/1993 | Thompson et al. |
| 5,281,428 A | 1/1994 | Morgan |
| 5,292,479 A | 3/1994 | Haraga et al. |
| 5,326,542 A | 7/1994 | Sizer et al. |
| 5,330,722 A | 7/1994 | Pick et al. |
| 5,334,248 A * | 8/1994 | Kwak |
| 5,334,913 A | 8/1994 | Ury et al. |
| 5,337,581 A * | 8/1994 | Lott |
| 5,352,467 A | 10/1994 | Mitchell et al. |

| | | |
|---|---|---|
| 5,376,265 A | 12/1994 | Szabo |
| 5,376,281 A | 12/1994 | Safta |
| 5,404,076 A | 4/1995 | Dolan et al. |
| 5,422,487 A | 6/1995 | Sauska et al. |
| 5,431,939 A | 7/1995 | Cox et al. |
| 5,433,920 A | 7/1995 | Sizer et al. |
| 5,439,652 A | 8/1995 | Sczechowski et al. |
| 5,443,863 A | 8/1995 | Neely et al. |
| 5,447,640 A | 9/1995 | Omi et al. |
| 5,470,597 A | 11/1995 | Mendenhall |
| 5,474,748 A | 12/1995 | Szabo |
| 5,482,726 A | 1/1996 | Robinson, Jr. |
| 5,484,549 A | 1/1996 | Hei et al. |
| 5,487,877 A | 1/1996 | Choi |
| 5,492,633 A | 2/1996 | Moniwa et al. |
| 5,500,979 A | 3/1996 | Worwag |
| 5,501,801 A | 3/1996 | Zhang et al. |
| 5,510,158 A | 4/1996 | Hiramoto et al. |
| 5,525,310 A | 6/1996 | Decker et al. |
| 5,536,400 A | 7/1996 | Schultz |
| 5,547,590 A | 8/1996 | Szabo |
| 5,547,635 A | 8/1996 | Duthie, Jr. |
| 5,552,112 A | 9/1996 | Schiffmann et al. |
| 5,557,112 A | 9/1996 | Csoknyai et al. |
| 5,565,685 A | 10/1996 | Czako et al. |
| 5,567,444 A | 10/1996 | Hei et al. |
| 5,578,113 A | 11/1996 | Glenn |
| 5,601,786 A | 2/1997 | Monagan |
| 5,604,339 A | 2/1997 | Tabatabaie-Raissi et al. |
| 5,614,151 A | 3/1997 | LeVay et al. |
| 5,614,723 A | 3/1997 | Oppenlander et al. |
| 5,616,172 A * | 4/1997 | Tuckerman et al. ............ 96/16 |
| 5,622,622 A | 4/1997 | Johnson |
| 5,626,769 A | 5/1997 | Sawamoto |
| 5,635,059 A | 6/1997 | Johnson |
| 5,655,242 A | 8/1997 | Morrow et al. |
| 5,656,063 A * | 8/1997 | Hsu |
| 5,656,246 A | 8/1997 | Patapoff et al. |
| 5,666,640 A | 9/1997 | Daniylchev |
| 5,689,798 A | 11/1997 | Oeste |
| 6,053,968 A * | 4/2000 | Miller ........................ 96/224 |
| 2002/0098109 A1 | 7/2002 | Nelson et al. |
| 2003/0039577 A1 | 2/2003 | Nelson et al. |

* cited by examiner

SYSTEM FOR PURIFYING AND REMOVING CONTAMINANTS FROM GASEOUS FLUIDS

CROSS REFERENCE TO RELATED APPLICATIONS

This application claims priority from U.S. Provisional Patent Application Ser. No. 60/468,655, filed May 8, 2003, and entitled "Apparatus and Method for Removing Contaminants from Gaseous Fluids". The disclosure of the foregoing patent application is incorporated herein by reference in its entirety.

BACKGROUND OF THE INVENTION

1. Technical Field

The present invention pertains to a system and corresponding methods for removing contaminants from a contaminated air stream. In particular, the present invention pertains to a method and apparatus for enhancing the exposure of a contaminated air stream to germicidal radiation to optimize removal of contaminants from that air stream.

2. Discussion of Related Art

Currently, there are numerous devices utilizing ozone, generated by ultraviolet (UV) radiation of air, to sanitize air in a treated space (i.e., typically a room). Many of these devices generate large amounts of ozone gas to facilitate sterilizing of the air. Since ozone concentration levels required for sterilization are sufficiently high to be dangerous to people and/or animals, the use of these devices is typically limited to deodorizers for odors for which removal is difficult (i.e., smoke from fires, organic material spilled on clothing, etc.). Further, when such ozone devices are used in the proximity of people and/or animals, health authorities require that ozone concentrations be reduced to safe levels. However, these reduced or "safe" levels tend to be too low to effectively deodorize and clean air, thereby rendering the ozone approach undesirable.

Some devices utilize the germicidal qualities of ultraviolet radiation in a particular frequency range to destroy bacteria in the air, but generally either expose the treated space to high levels of radiation, thereby posing health risks to people and/or animals, (such as eye trauma and skin lesions), or use very low levels of radiation requiring low air flow rates to permit the air to be exposed to the radiation in the device over long exposure times. Long exposure times render the devices inefficient in that they lengthen the "turnover" time of room air (i.e., the time required to treat an entire room with the germicidal radiation). It is evident that long turnover times minimize the effectiveness of the device in that the room air can be re-contaminated before the device is able to sanitize all of the air in the room.

Inefficiency and ineffectiveness in prior art UV room air sanitizers are also caused by not properly mixing the air flowing through the device. In this regard, prior art devices typically utilize, and even strive for, laminar air flow through those devices. This limits the effect of exposure to UV radiation to the portions of the laminar flow closest to the UV bulb. In this regard, designers of prior art devices show little or no recognition of the decrease in UV radiation intensity as a function of distance from the UV source. It is desirable, therefore, to maximize proximity of the entire flowing air stream to the UV source. Apart from the laminarity of the air flow, other flow parameters, not considered in the prior art, must be addressed to optimize the exposure of the air to UV radiation in an air purifier to maximize the purification or "killing" effects of the radiation.

Changing UV source bulbs in prior art room sanitizers presents numerous problems, not the least of which is danger to the consumer should the difficult-to-access UV bulb break during the removal or insertion process. It is desirable to provide an efficient air purifier wherein the UV radiation source is readily and safely replaced.

SUMMARY OF THE INVENTION

Accordingly, it is an object of the present invention to remove contaminants from air within a treated space by maximizing the exposure of a flowing air stream to UV radiation while minimizing the time to treat all of the air in the treated space and without leaking ultraviolet radiation into the surrounding environment.

It is another object of the present invention to reduce costs and minimize the size of an ultraviolet radiation chamber in a system for removing contaminants from a contaminated air stream.

Another object of the invention is to optimize air flow parameters in a UV germicidal chamber of an air purifier to increase germicidal efficiency.

It is still another object of the present invention to provide an air purifier using germicidal radiation in which air flow through the purifier is treated to optimize turbulence in the air flowing into the UV germicidal chamber.

It is a further object of the present invention to increase the dwell time of the air in the chamber and to direct the air into maximally close proximity to the UV source.

Still another object of the present invention is to remove contaminants from a contaminated air stream via a system having a bulb holder configured to facilitate removal and placement of a UV radiation emitting bulb within the system interior.

A further object of the present invention is to provide an air purifier with a unique baffle arrangement to impart turbulence in, and to increase the dwell time of, air flowing through a UV chamber.

It is another object of the present invention is to utilize replaceable cartridges with a system for removing contaminants from an air stream to facilitate versatility and easy maintenance of the system.

The aforesaid objects are achieved individually and in combination, and it is not intended that the present invention be construed as requiring two or more of the objects to be combined unless expressly required by the claims attached hereto.

In accordance with the present invention, a system for purifying and removing contaminants from gaseous fluids includes a housing including an inlet, an outlet, and an elongated UV chamber disposed within the housing. The UV radiation source is disposed longitudinally within the UV chamber. At least one baffle structure is disposed at an upstream location within the housing to restrict flow as well as to generate a turbulent flow of the gaseous fluid within the UV chamber. In addition, a fan is disposed at a selected location within the housing to facilitate a flow of the gaseous fluid through the housing at a selected flow rate. The dimensions of the UV chamber and UV source and the configuration of the baffle structure are selected to increase the exposure time and mixing of fluid flowing through the UV chamber as well as increase the proximity of the flowing fluid to the UV source.

Preferably, a hollow cartridge is disposed within and removable from the housing, where the UV chamber is defined and the UV source is disposed within the hollow cartridge. In one embodiment, the cartridge includes an end cap disposed at a downstream end of the cartridge, and the end cap includes a support structure that supports a downstream end of the UV source within the cartridge.

Preferably, the UV source includes a plurality of elongated UV bulbs oriented in a selected configuration within the UV chamber to provide a flow path for the fluid between the UV bulbs and internal wall surface portions of the UV chamber as well as at least one flow path between adjacent bulbs. In an exemplary embodiment, the UV source includes three elongated UV bulbs arranged at 120° spaced locations from a central axis defined between and extending parallel to the UV bulbs.

The above and still further objects, features and advantages of the present invention will become apparent upon consideration of the following detailed description of specific embodiments thereof, particularly when taken in conjunction with the accompanying drawings wherein like reference numerals in the various figures are utilized to designate like components.

BRIEF DESCRIPTION OF THE DRAWINGS

FIG. 4B is a cross-sectional view of the downstream end cap of FIG. 4a.

DESCRIPTION OF THE PREFERRED EMBODIMENTS

Figure 1:
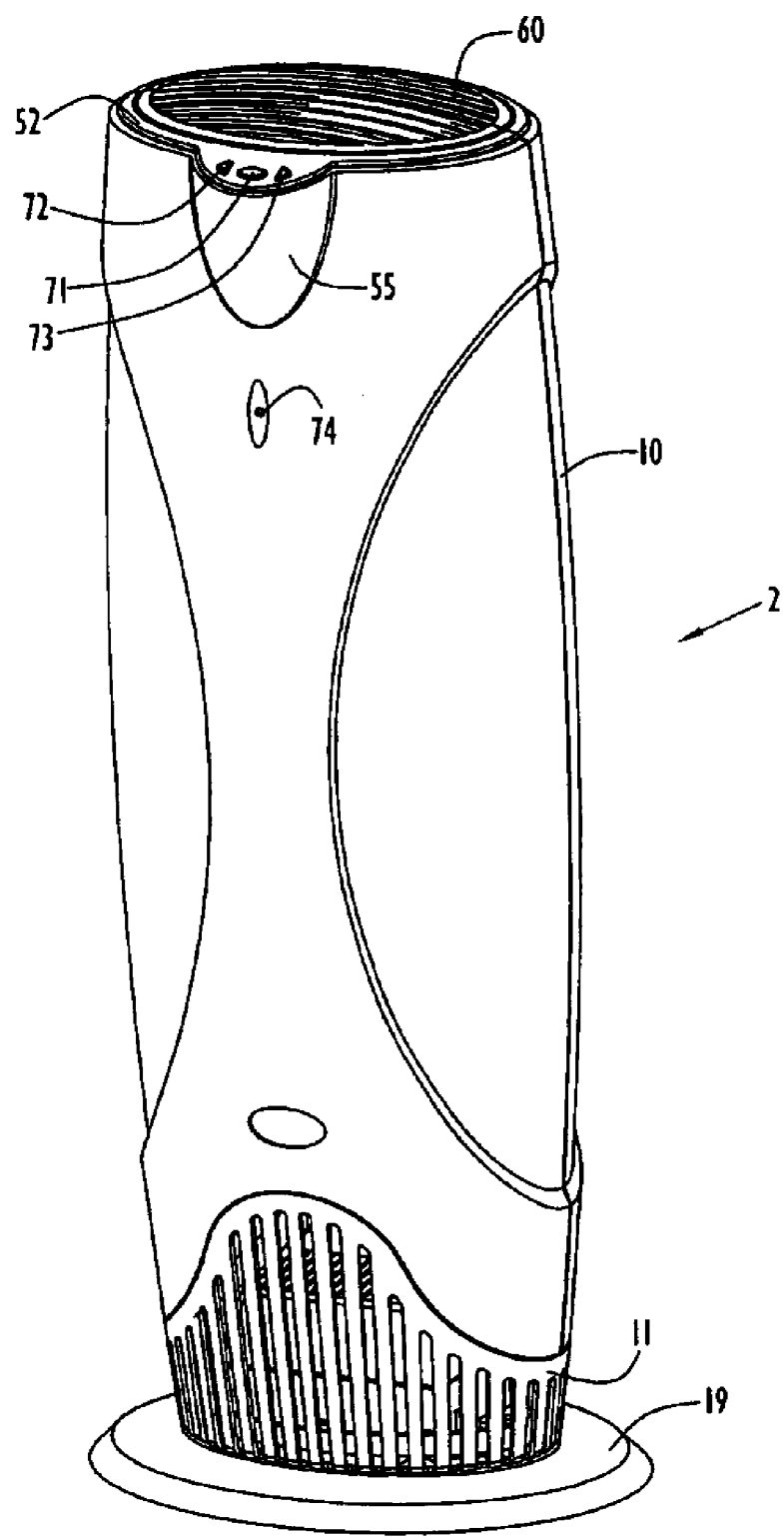
FIG. 1 is a perspective view of an air purification system in accordance with the present invention.

According to the present invention, and referring generally to the attached drawings, a system for removing contaminants from a contaminated air stream is accomplished by drawing a stream of air into the inlet end of an elongated system housing that includes a replaceable cartridge in which one or more ultraviolet radiation bulbs are mounted. The bulbs emit an ultraviolet radiation that effectively purifies the air by destroying bacteria, viruses, mold spores and/or other microorganisms entrained in the air. The system further includes a baffled structure at the upstream and/or downstream ends of the housing to impart a sufficient amount of turbulence to the air as it passes through the housing as well as a filter member to remove particulate material entrained in the air. The terms "upstream" and "downstream", as used herein in relation to the housing or other components of the system, respectively refer to locations at or near the inlet and outlet of such components. In addition, the terms "upstream direction" and "downstream direction", as used herein, respectively refer to directions oriented from the outlet to the inlet and from the inlet to the outlet with respect to a particular system component.

An exemplary embodiment of the present invention is depicted in FIGS. 1–7. The system 2 includes an elongated housing 10 that contains an internally mounted and generally cylindrical chassis 15, 16. The chassis 15, 16 contains a removable and replaceable cartridge 20 in which ultraviolet radiation bulbs 21 are mounted. The bulbs are preferably elongated cylindrical ultraviolet (UV) bulbs having suitable dimensions and oriented longitudinally within a circle of a selected diameter within the cartridge with their axes oriented parallel to the direction of net air flow through the housing. While the exemplary system includes three UV bulbs (FIG. 3), it is noted that any selected number of bulbs of any suitable sizes and/or geometries may be utilized depending upon the intensity of UV radiation required for a particular application. The upstream and downstream ends of the bulbs are thinned into a tab-like configuration to fit within receiving holes or slots disposed on bulb mounting members located at or near the upstream and downstream ends of the cartridge 20 as described below.

An intake grill 11 and fan 12 are disposed at the upstream end of the housing. Alternatively, the fan may be located at the downstream end to draw, rather than push, air through the housing. The fan 12 is preferably a direct current or DC fan with an adjustable operating speed that is selectively controlled by a user during system operation as described below. Alternatively, the fan can also be an alternating current or AC fan.

The UV bulbs 21 are powered by an electronic ballast 17 in a manner described below. The ballast 17 may be powered by an AC power source (e.g., for use in stationary operation), or alternatively, a DC power source (e.g., when connected to a battery to enable the system to be portable and used in mobile environments such as cars, boats, trucks, trailers, etc.). An electronics housing 18, secured to the housing base 19, contains the system electrical and electronics components, including the ballast 17 for the UV bulbs 21, a processor, a power supply, and related electronic circuitry (indicated generally as element 23 in FIG. 2). As can be seen in the exploded view of FIG. 2, the electronics housing 18, fan 12, and cartridge 20 are arranged in a stacked relationship at the upstream end of the housing 10 when the apparatus is completely assembled. The base 19 serves as a stand that permits the unit to be positioned anywhere on a floor in a room. Alternatively, the unit may be configured for mounting on or installation within a wall or ceiling.

The housing is preferably constructed of injection molded plastic including two substantially symmetrical halves 13, 14 externally contoured to provide an attractive appearance. Alternatively, the housing may be constructed of foam having a plastic or other suitable rigid covering. Likewise, the hollow chassis is preferably constructed of foam or molded plastic including two substantially symmetrical halves 15, 16. The fan 12 is mounted between the halves 15, 16 near the upstream end of the chassis. Alternatively, the chassis may be constructed of a single molded foam piece configured to receive the fan 12 and cartridge 20 by insertion of these components into the chassis at its upstream and/or downstream ends.

The front half 13 of the housing includes inwardly projecting ribs 90 to contact the exterior surface of the chassis so as to serve as support spacers for positioning the chassis in a substantially centered orientation within the housing, preferably in coaxial orientation with the housing. Alternatively, ribs may be disposed on both halves of the housing and/or on the exterior surface of the chassis to facilitate the appropriate positioning of the chassis within the housing.

The cartridge 20 has a generally cylindrical configuration and is preferably constructed of a suitable opaque material to substantially limit or prevent UV radiation emitted within the cartridge from penetrating through the cartridge shell 22. Most preferably, the cartridge is constructed of aluminum or any other suitable reflective material (e.g., stainless steel) to provide reflective surfaces within the cartridge for reflecting UV radiation at varying angles from the internal walls of the cartridge shell during system operation. The cartridge can be formed in any suitable manner including, without limitation, by extrusion so as to form a single integral piece, utilizing a single sheet with its longitudinal ends combined and riveted or bonded together, providing symmetrical halves that are riveted or bonded together, and/or combining two or more cylindrical sections together at their ends. Three parallel-mounted UV sources or bulbs 21 are mounted in the cartridge, preferably at substantially equidistant distances from each other. The germicidal UV radiation sources generate radiation having a wavelength in the range of approximately 254 nanometers, which is known to inactivate the DNA/RNA of and/or to destroy bacteria, viruses, mold spores and the like. However, any other suitable wavelength may be utilized for the UV radiation sources that is effective in providing a desired kill rate. The cartridge 20 is mounted in coaxial orientation with the chassis and is adapted to be periodically replaced in a manner described below, thereby facilitating versatility and easy maintenance of the system.

Figure 3:
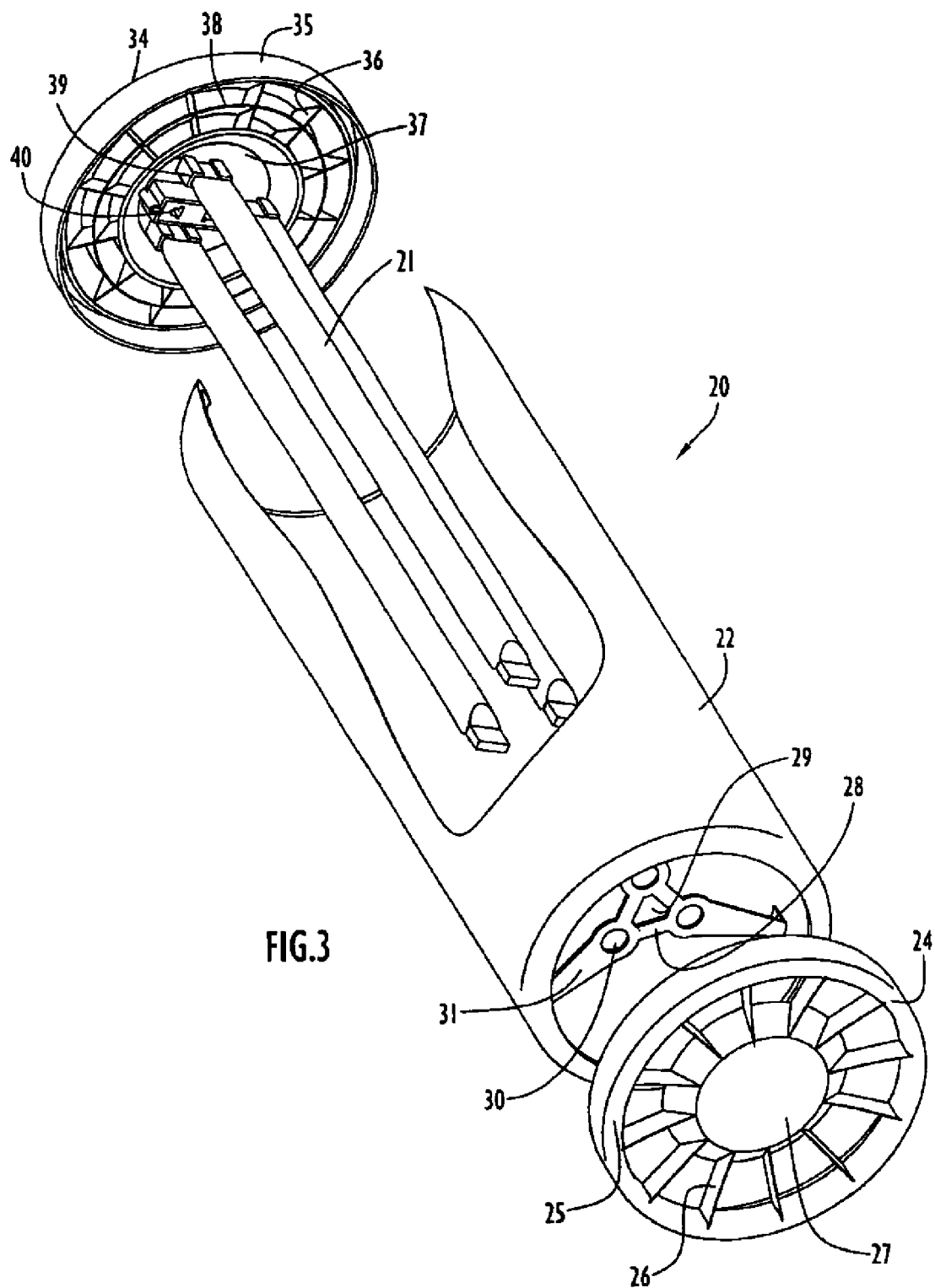
FIG. 3 is an exploded view in perspective including a cut away section of the cartridge of the system of FIG. 1.
Figure 4A:
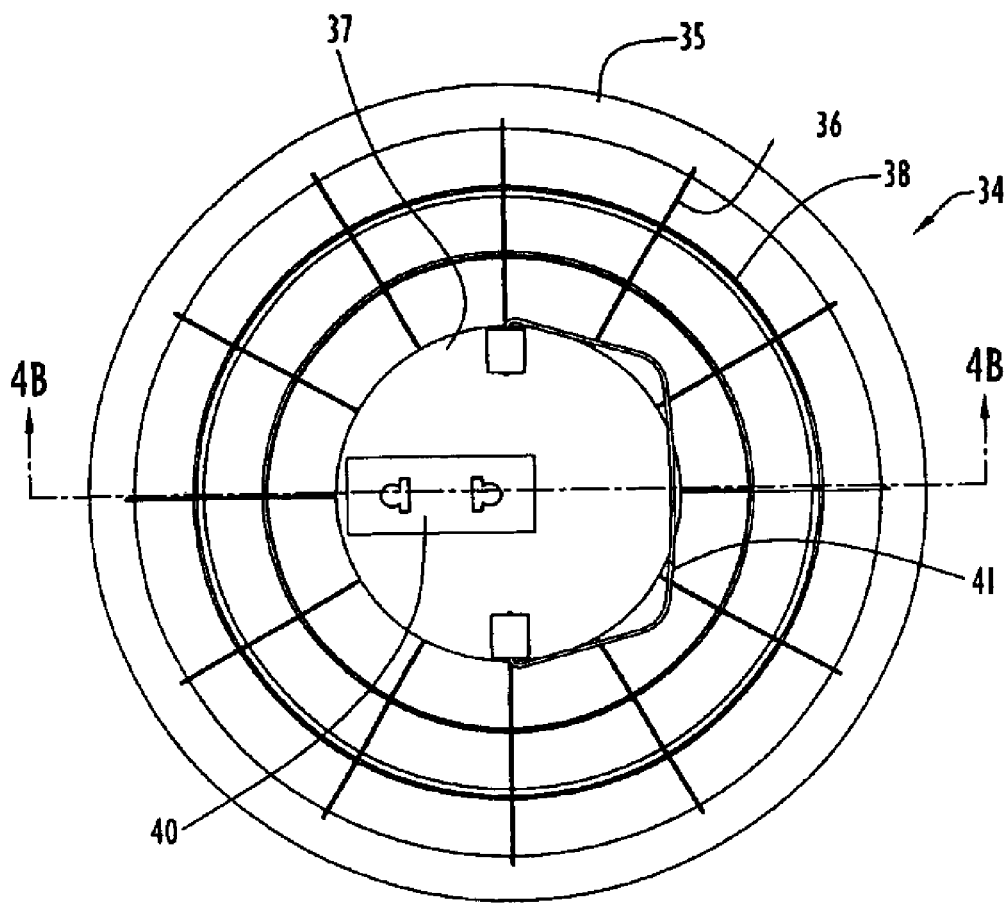
FIG. 4A is a top view in plan of the downstream end cap of the cartridge of FIG. 3.
Figure 4B:
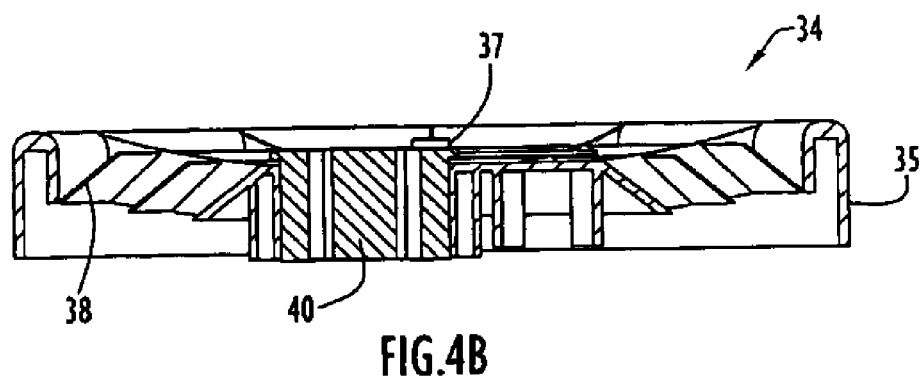

Referring to FIGS. 3 and 4A–4B, the ends of the cartridge 20 include generally circular end caps 24, 34 mounted thereon. The upstream end cap 24 includes an outer ring member 25 with a series of support struts 26 extending radially inward from the ring member 25 (e.g., like spokes of a wheel) and connecting with a central and generally circular plate 27 disposed at a central location within the ring member 25. Each strut 26 includes a shorter dimension or width that extends between the top and bottom ends of the end cap 24. A bulb mounting plate 28 is mounted within and near the upstream end of the cartridge via struts 31. The mounting plate 28 has a generally triangular configuration and includes an opening 29 at its center. Three openings or slots 30 are defined in the mounting plate 28 and angularly displaced from each other by approximately 120°. The slots 30 are further defined at locations equidistant from the central opening 29. The slots 30 are suitably dimensioned and aligned in this configuration to receive and retain the upstream tab-like ends of the bulbs 21. Support struts 31 extend outwardly from the mounting plate slots 30 toward the cartridge shell 22. Each strut 31 includes a tab member that extends in a downstream direction within the cartridge and engages an internal surface portion of the cartridge shell 22. The tab members are secured to the cartridge shell 22 in any suitable manner (e.g., via pop rivets, screws, etc.).

The end cap 24 and the mounting plate 28 serve as baffles at the upstream end of the housing 10 for air flowing into the cartridge 20. In particular, air flows into the cartridge through the openings defined between the outer ring 25, the struts 26, and the plate 27 of the end cap 24, through opening 29 and additional openings formed between the struts 31 of the mounting plate 28. These components of the end cap 24 and mounting plate 28 provide obstructions that serve to restrict air flow as well as cause mixing and turbulent flow of the air as it passes into the cartridge. Upon passing the upstream end cap 24 and mounting plate, the air flows within the cartridge toward the downstream end cap 34 in the space provided between the bulbs 21 and the cartridge shell 22 as well as the spaces located between bulbs 21.

Referring to FIGS. 3, 4A and 4B, the downstream end cap 34 includes an outer ring member 35 with a series of support struts 36 extending radially inward from the ring member 35 (e.g., like spokes in a wheel) and connect with a central and generally circular plate 37 disposed at a central location within the outer ring member 35. The width of each strut 36 extends between the top and bottom ends of the end cap. A handle 41 is pivotally secured on the top surface of the plate 37 to allow easy removal of the cartridge 20 from the system housing by gripping the handle.

A series of concentrically aligned and hollow rings or baffles 38 having angled surfaces that define a frusto-conical geometry for each baffle are disposed between the outer ring member 35 and the plate 37 and are supported by the struts 36, thus forming a "bullseye" pattern when viewing the upper (i.e., outlet) end of the end cap 34 as depicted in FIG. 4A. In addition, a third baffle 38 extends from the bottom surface of the plate 37 and has the same frusto-conical geometry as the other baffles 38. Each of the baffles 38 extends between the top and bottom surfaces of the end cap 34, where the diameter of each baffle 38 increases in an upstream direction of the end cap 34. In other words, the baffles 38 extend radially outward from the plate 37 to the ring member 35 and in a direction from the top or outlet surface to the bottom or inlet surface of the end cap 34. In the embodiment of FIGS. 4A and 4B, the angled surface of each baffle 38 extends at an angle of about 45° from a plane that intersects the baffles and is parallel with plate 37.

The circular plate 37 includes three elongated mounting slots 39 angularly displaced from each other by approximately 120° and defined at locations equidistant from the center of the plate. The slots 39 are suitably dimensioned and aligned in this configuration on the mounting plate to receive and retain the downstream tab-like ends of the bulbs 21. The plate 37 also includes an electrical receptacle 40 that extends through the plate and is configured to releasably engage (e.g., in a male/female mating relationship) with an electrical plug (not shown). The plug extends along the chassis 15,16 and connects with the ballast 17 in order to electrically connect the bulbs 21 with the electronic ballast 17. The receptacle 40 further includes terminals disposed at the bottom end of the plate 37 that connect via electrical wiring (not shown) with corresponding terminals disposed at the upstream and downstream ends of the bulbs 21. Specifically, two wires extend from both the upstream and downstream end terminals of each bulb to the terminals of the receptacle 40 (i.e., a total of four wires extend for each bulb to the receptacle 40). Thus, the receptacle 40 facilitates disengagement of the bulbs from the ballast 17 to permit removal of the cartridge 20 from the system housing.

Figure 2:
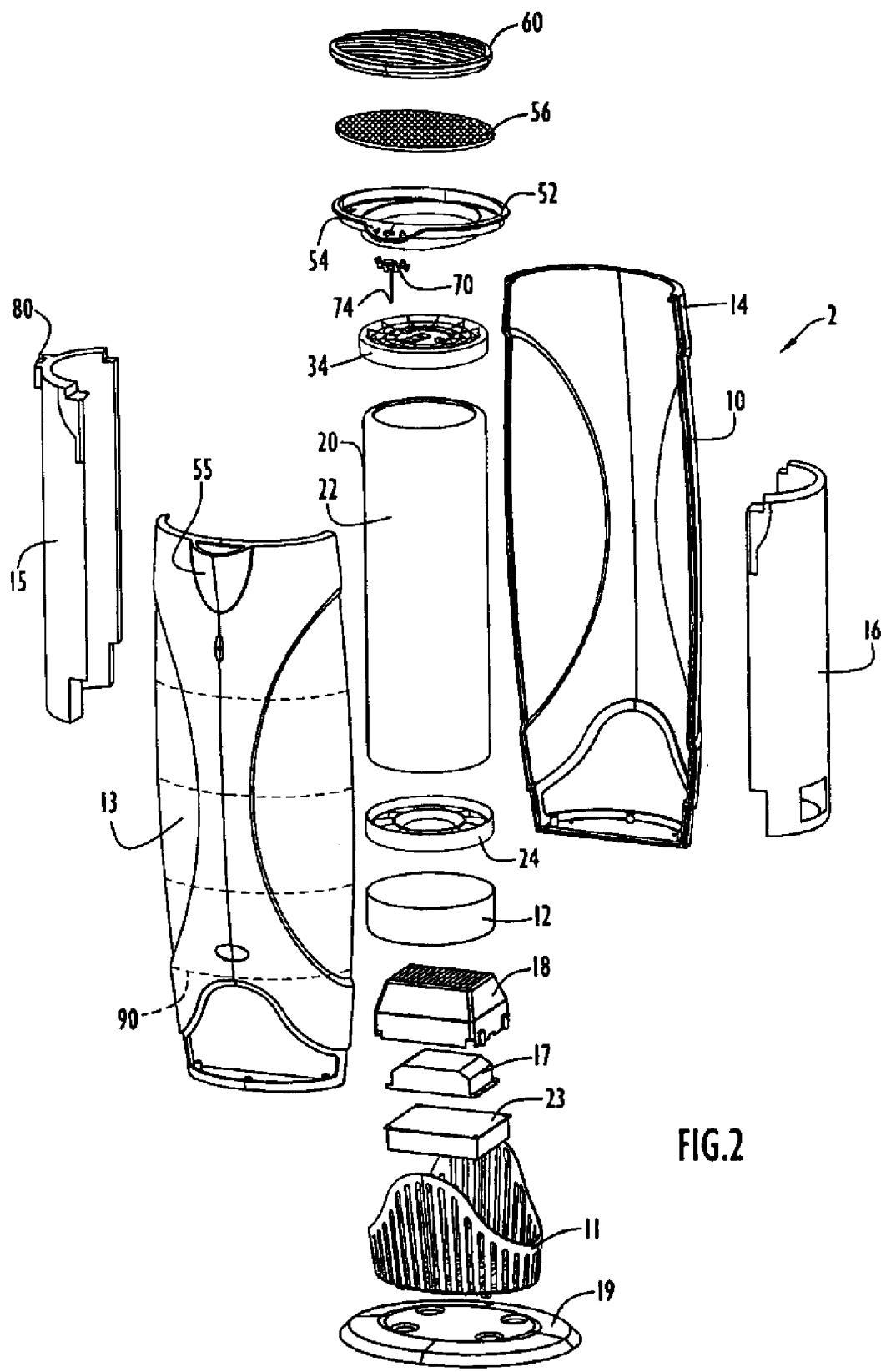
FIG. 2 is an exploded view in perspective of the system of FIG. 1.

Ultraviolet emissions from the bulbs 21 are prevented from escaping the system housing and causing damage to persons and animals viewing the unit at both the upstream and downstream ends of the housing. This blocking function is achieved at the upstream end by appropriate positioning of the fan 12, the electronic housing 18 and the intake grill 11 in the stacked configuration as depicted in FIG. 2.

At the downstream end, light blocking is effectively achieved by at least the combination of the downstream end cap 34 of the cartridge 20 and an outlet grill 60 that connects to the downstream end of the housing 10. Referring to FIGS. 2 and 5–7, the downstream end of housing 10 includes a bezel 52 having a generally cylindrical section that fits within the openings of the upper or downstream ends of the housing 10 and chassis 15, 16 and a generally oval upper lip portion that rests on the upper edge surface of the housing 10. The bezel 52 is hollow and has an internal surface diameter that is sufficiently dimensioned to permit coaxial displacement of the cartridge 20 with respect to the bezel 52 to facilitate removal of the cartridge while the bezel remains mounted to the housing 10. The bezel 52 further includes a rounded lip extension 54 that corresponds with a pocket 55 disposed at the downstream end on the front half 13 of the housing 10. The pocket 55 is suitably dimensioned to receive a button tree 70 that includes buttons to power the system and control operation of the fan 12 as described below. The lip extension 54 of the bezel 52 includes openings to receive the buttons of the button tree and provide access for operation by a user. The bezel 52 is firmly secured to the housing 10 in any suitable manner (e.g., via pop rivets, threaded screws, a snap-tight connection, etc.).

The internal surface of the bezel 52 includes a first step or ledge 53 that is suitably dimensioned to receive and retain a particulate filter 56. The filter 56 can be secured in any suitable manner against ledge 53 (e.g., via tabs extending inwardly from bezel surface portions that secure the filter 56 against the ledge 53 in a snap fitting relationship). The filter 56 may be a HEPA or any other suitable type of particulate filter to facilitate removal of particulate material of selected dimensions entrained in the air.

Optionally, the filter may be coated with a photocatalyst and/or a photocatalyst support structure (e.g., in the form of a disk or substrate) may be provided in the bezel or at a location upstream from the bezel (e.g., within the housing and/or chassis) to effectively reduce odors and/or remove any volatile organic compounds (VOC's) entrained in the air stream. It is noted that the UV bulbs utilized in the system block the formation of ozone in that the bulbs do not emit light at a wavelength known to produce large amounts of ozone. However, a suitable photocatalyst may also be provided to convert any ozone that may be generated within the cartridge (e.g., even small amounts) to oxygen prior to leaving the system. Any suitable photocatalyst may be utilized (e.g., titanium dioxide) to decompose ozone to oxygen at a suitable and effective reaction rate.

The bezel 52 further includes a second ledge 58 disposed along its interior surface at a location between the upper or outlet end of the bezel and the first ledge 53. The second ledge 58 receives and retains the outlet grill 60 when the outlet grill is engaged with the bezel 52. The outlet grill 60 is secured to the bezel 52 in any suitable manner (e.g., via threaded screws, a snap-tight connection, etc.) to facilitate easy removal of the outlet grill when the cartridge 20 needs to be removed from the housing 10 (e.g., to replace the bulbs 21).

Figure 5:
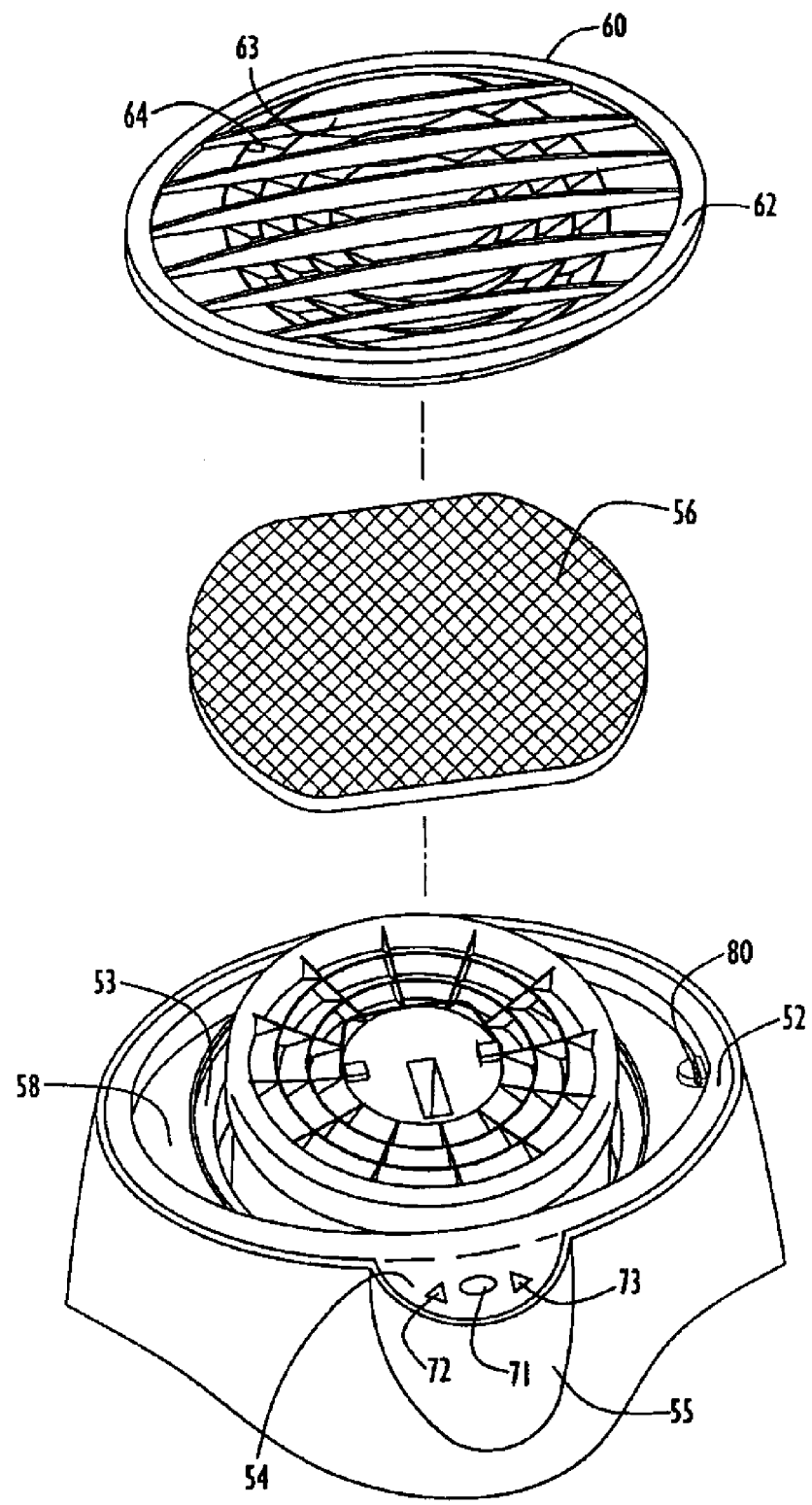
FIG. 5 is an exploded view of the downstream end of the system of FIG. 1, including the bezel, filter and outlet grill.
Figure 6:
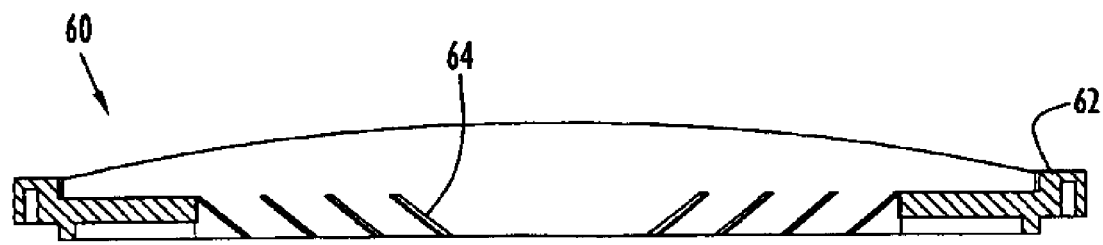
FIG. 6 is a cross-sectional view of the outlet grill of the system of FIG. 1.
Figure 7:
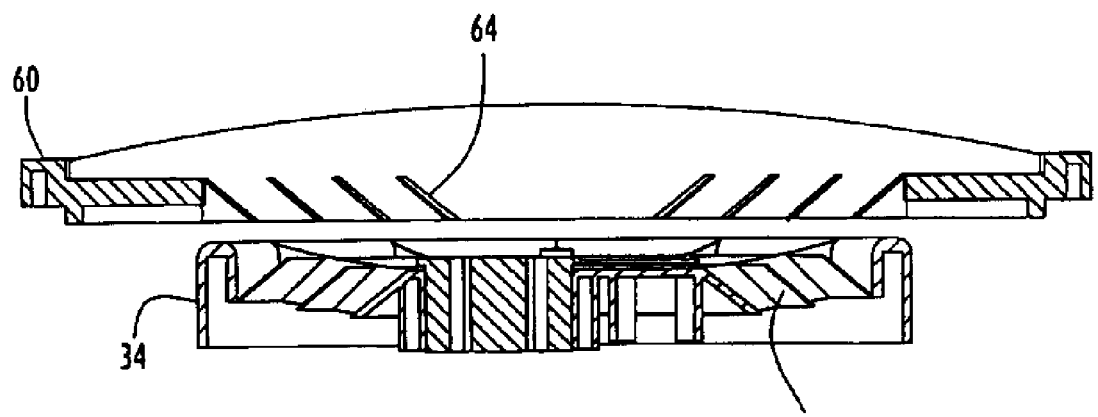
FIG. 7 is a cross-sectional view of the outlet grill combined with the downstream end cap of the cartridge of FIG. 1.

The outlet grill 60 includes an outer ring member 62 that has a generally oval configuration corresponding with the upper lip portion of the bezel 52. A series of struts 63 extend between inner peripheral surface portions of the outer ring member 62 in the longitudinal dimension of the grill 60. The width of each strut 63 extends between the top (i.e., outlet end) and bottom (i.e., inlet end) surfaces of the grill. A series of concentrically aligned and hollow rings or baffles 64 having angled surfaces that define a frusto-conical geometry for each baffle are also disposed within the outer ring member interior and are supported by the struts 63. Each of the baffles 64 extends between the top and bottom surfaces of the grill 60, where the diameter of each baffle 64 increases in a downstream direction of the grill 60. In other words, the baffles extend radially outward from a central axis of the grill 60 toward the outer ring member 62 and in a direction from the bottom surface to the top surface of the grill 60. In the embodiment of FIGS. 5 and 6, the angled surface of each baffle 64 extends at an angle of about 45° from a plane that intersects the baffles and is parallel with the grill 60.

The combination of the outlet grill 60 and cartridge end cap 34 (as depicted in the cross-sectional view of FIG. 7) substantially limits or prevents any UV radiation that is generated within the UV chamber defined within the cartridge 20 from escaping the housing 10. In particular, it is noted that the frusto-conical baffles 64 of the outlet grill 60 are angled in an opposing orientation with respect to the frusto-conical baffles 38 of the cartridge end cap 34 when the system is completely assembled, so that the combination of the two sets of baffles provides a blocking feature for UV light. For example, while light emissions from the UV chamber that are generally parallel with the baffles 38 of the end cap 34 may emerge from the cartridge 20, these light emissions will be substantially blocked or prevented from passing the grill 60 due to the baffles 64, which are oriented at an opposing angle with respect to the end cap baffles 38. In addition, one or both sets of baffles of the end cap and outlet grill may be provided with reflective surfaces facing the upstream direction within the housing 10 to further prevent escape of UV radiation from the housing. The combination of baffles of the cartridge end cap and outlet grill further provides a tortuous or winding flow path for air flowing through the system at the downstream end of the housing. The resultant winding flow path that is formed at the downstream end generates eddies and backflow currents to increase residence time for the air within the chamber of the cartridge 20.

The ballast 17 controls on-off operation of the UV sources, and the electronics housing 18 includes a processor and related circuitry to control appropriate indicators such as lamps, LCD and/or LED displays, audio signals, etc., that provide information regarding the operating status of the unit. In addition, the circuitry includes safety features that shut the unit down under prescribed conditions.

In the embodiment of FIGS. 1–7, the system 2 includes a button tree 70 supported in the pocket 55 of the housing 10, with three control buttons 71, 72, 73 extending from the button tree and aligned with corresponding openings in the lip extension 54 of the bezel 52. The button tree is connected to the electronics housing 18 via suitable wiring that extends along a wall portion of the chassis 15, 16 in a longitudinal direction. The button tree is further connected via a wiring harness to an LED indicator 74 that extends through an opening of the front half 13 of the housing 10 to permit wiring from the LED indicator to connect with the electronics housing 18 in a similar manner as the button tree. The LED indicator 74 is disposed at a suitable location between the pocket 55 and the upstream end of the housing. Control button 71 is a power button that serves as an on/off switch for operation of the fan 12 and electronic ballast 17, while control buttons 72 and 73 effectively increase or decrease the speed of the fan in selected increments. The fan is preferably controlled by DC voltage and can be adjusted to any selected number of speeds (e.g., sixteen speeds or infinite variable speeds).

The LED indicator is preferably a tri-color indicator that is controlled by a processor disposed in the electronics housing 18. In particular, the LED indicator illuminates in green, orange and red display colors to provide a number of operational conditions to the user during system operation including, without limitation: providing a steady green display when the unit is operating under normal conditions and the bulbs have greater than 10% of anticipated life expectancy (e.g., each bulb may be rated with an anticipated life expectancy of about 8,800 hours of use); providing a steady orange display when the unit is operating under normal conditions and the total time of usage of the bulbs is at or above 90% of the anticipated life expectancy for the bulbs; providing a steady red display when the fan will not run or the bulbs will not operate (e.g., due to the usage time exceeding the anticipated life expectancy for the bulbs or an indication that one or more of the bulbs is not operational); providing an alternating red and green display in a blinking manner to indicate that no cartridge is detected within the housing and/or the outlet grill is not properly mounted; providing a single red blinking display to indicate a bulb and/or ballast failure; and providing a red double blinking display to indicate a service is required (e.g., the fan is not working). The actual operating or usage time of the bulbs can be recorded by the processor or, alternatively, by a non-volatile random access memory (NovRam) storage device provided in the cartridge 20 that communicates in any suitable manner (e.g., via electrical wiring) with the processor.

As noted above, one of the operational conditions that is provided by the LED indicator 74 is a notification to the user that the outlet grill 60 is not properly mounted to the housing 20. Such an indication is achieved by providing a mechanical interlock switch 80 that is disposed at the downstream end of the chassis 15, 16. The interlock switch 80 is connected via appropriate electrical wiring to the electrical circuit including the fan 12 and ballast 17 and extends through an opening disposed at the outer peripheral edge of the second ledge 58 of the bezel 52. The switch 80 is resiliently biased to an open position to prevent power from being supplied to the fan and the ballast unless the outlet grill 60 is properly secured in the bezel 52. When the outlet grill 60 is secured to the bezel 52 in the manner described above, the switch 80 is depressed toward the cartridge 20 to close the circuit and enable power to be supplied to the fan and ballast.

Figure 8:
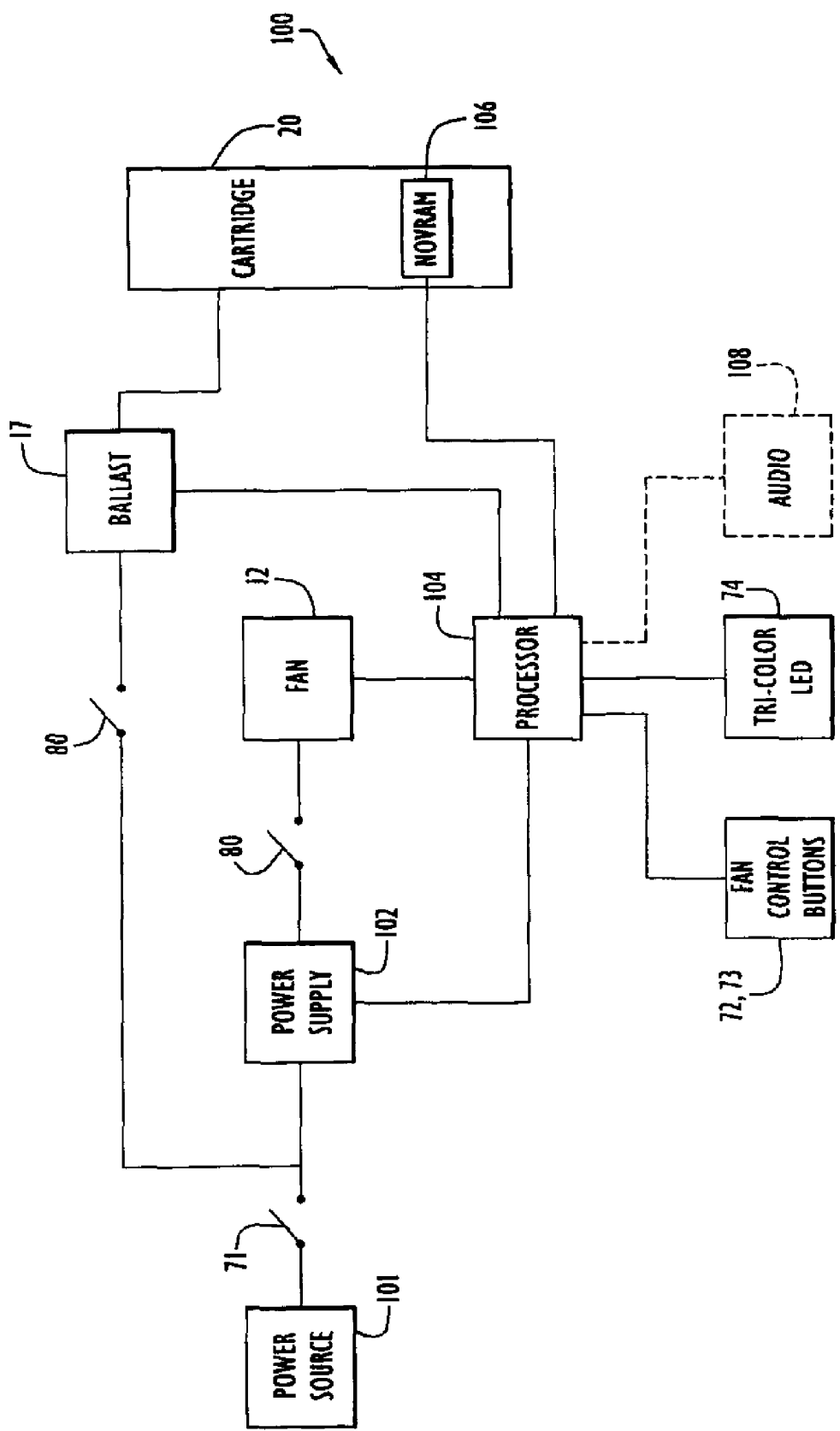
FIG. 8 is a schematic of a block diagram for a control circuit for the system of FIG. 1.

An exemplary control circuit that can be integrated in the electronics housing 18 to control various system functions and operations is depicted in FIG. 8. Specifically, circuit 100 includes a power supply 102 that connects with an AC power source 101 (e.g., a plug to a wall outlet). Alternatively, as noted above, the system can also be configured to receive power from a DC power source (e.g., a battery). The power supply 102 is connected with a processor 104 and the fan 12 to convert AC power received from the power source 101 to DC power delivered to the processor and fan. Alternatively, if the fan is configured to receive AC power, the fan may be connected directly in-line with the power source 101 (i.e., bypassing the power supply 104). The ballast 17 connects within the circuit between the power source 101 and the bulbs 21 disposed in the cartridge 20. The processor 104 is also connected to the ballast 17, the fan 12, a NovRam device 106 disposed within the cartridge 20, the LED indicator 74, and fan control buttons 72 and 73. Optionally, the processor 104 may also be connected with an audio signal device 108 and/or any other system indicator devices (e.g., an LCD display).

The system power switch 71 is connected at a suitable location in the circuit between the power source 101 and the connection points with the power supply 102 and the ballast 17. In addition, the interlock switch 80 is disposed in the circuit at the connection between the power supply 102 and the fan 12 and the connection between the power source 101 and the ballast 17.

In operation, the power switch 71 is manipulated to enable power to be supplied from the power source 101 to the ballast 17 and from the power supply to the fan 12 and processor 104. Air is caused to flow into and through the housing 10 by the fan 12. The incoming air is directed into the cartridge 20 and is initially redirected and perturbed by struts 26 and plate 27 in end cap 24. The portions of the stream flowing past the circumferential edge of plate 27 and past the struts 26 create vortical or eddy components that introduce turbulence into the overall flow. The flow net cross-sectional area through end cap 24 is smaller than the flow cross-section immediately upstream of the end cap, so that there is a net flow restriction and reduction in flow rate.

The airstream then travels within UV chamber of the cartridge 20, flowing in the passage defined between the interior of the cartridge shell 22 and the UV bulbs 21 as well as between the UV bulbs, where exposure to UV radiation from the bulbs effectively kills bacteria, spores, viruses, etc. entrained in the air stream. As the air passes through the downstream end of the system, the combined frusto-conical baffling of the end cap 34 and the outlet grill 60 substantially limits or prevents UV light from escaping the housing 20 while creating a tortuous or winding flow path for the air flow, which increases residence time and generates eddies and backflow currents of the air stream within the cartridge. The filter 56 filters particulate material from the air stream before leaving the system. In addition, the filter 56 provides additional flow restriction for the air to increase residence time within the UV chamber.

The user can selectively control the fan speed to various faster and slower speed settings (e.g., sixteen or more control settings) by depressing buttons 72 and 73. The processor 104 receives signals from the fan control buttons 72 and 73 and controls the fan speed accordingly. In addition, the processor controls the LED indicator 74 to display one or more color indications as described above based upon existing operating conditions. The processor 104 further communicates with the ballast 17 to sense current drawn by the ballast in order to determine whether all UV bulbs 21 are operating. If one or more lamps fail, the processor 104 controls the ballast 17 to shut down power to the ballast and fan 12 and controls the LED indicator 74 to provide a suitable signal indication (e.g., blinking red light) that bulbs need to be replaced. The processor 104 further communicates with the NovRam device 106 to determine how long the bulbs 21 have been in used and determines whether such usage time is approaching a predetermined remaining bulb life expectancy value (e.g., about 8,800 hours of bulb usage). The LED indicator 74 is controlled by the processor to provide an appropriate light indication, as indicated above, when the bulb usage time is approaching or has exceeded the anticipated bulb life expectancy.

Removal of the cartridge 20 for replacement of one or more bulbs and/or providing a new cartridge to the system is achieved by first removing the outlet grill 60 and filter 56 from their engagement with the bezel 52. Removal of the outlet grill 60 results in the opening of the interlock switch 80. If the user has not manually shut the power off to the system, power will be shut down to the fan 12 and ballast 17, thus preventing the bulbs from operating while the grill is removed. In such a situation (i.e., when the power switch 71 is still on), the LED indicator 74 is controlled by the processor 104 to provide an appropriate signal, as indicated above, that notifies the user that the grill 60 is not secured to the bezel 52.

Once the outlet grill and the filter have been removed, the electrical plug connecting the ballast 17 to the bulbs 21 is disengaged from the receptacle 40 disposed in the downstream end cap 34 of the cartridge 20. The cartridge 20 is then removed by the user, using the handle 41, from the system housing 10. One or more bulbs may be replaced in the cartridge or, alternatively, a new cartridge may be provided for the system. Upon replacement of a cartridge into the housing, engagement of the electrical plug with the receptacle 40, and installation of the filter and outlet grill, the system is again ready for use.

Figure 9:
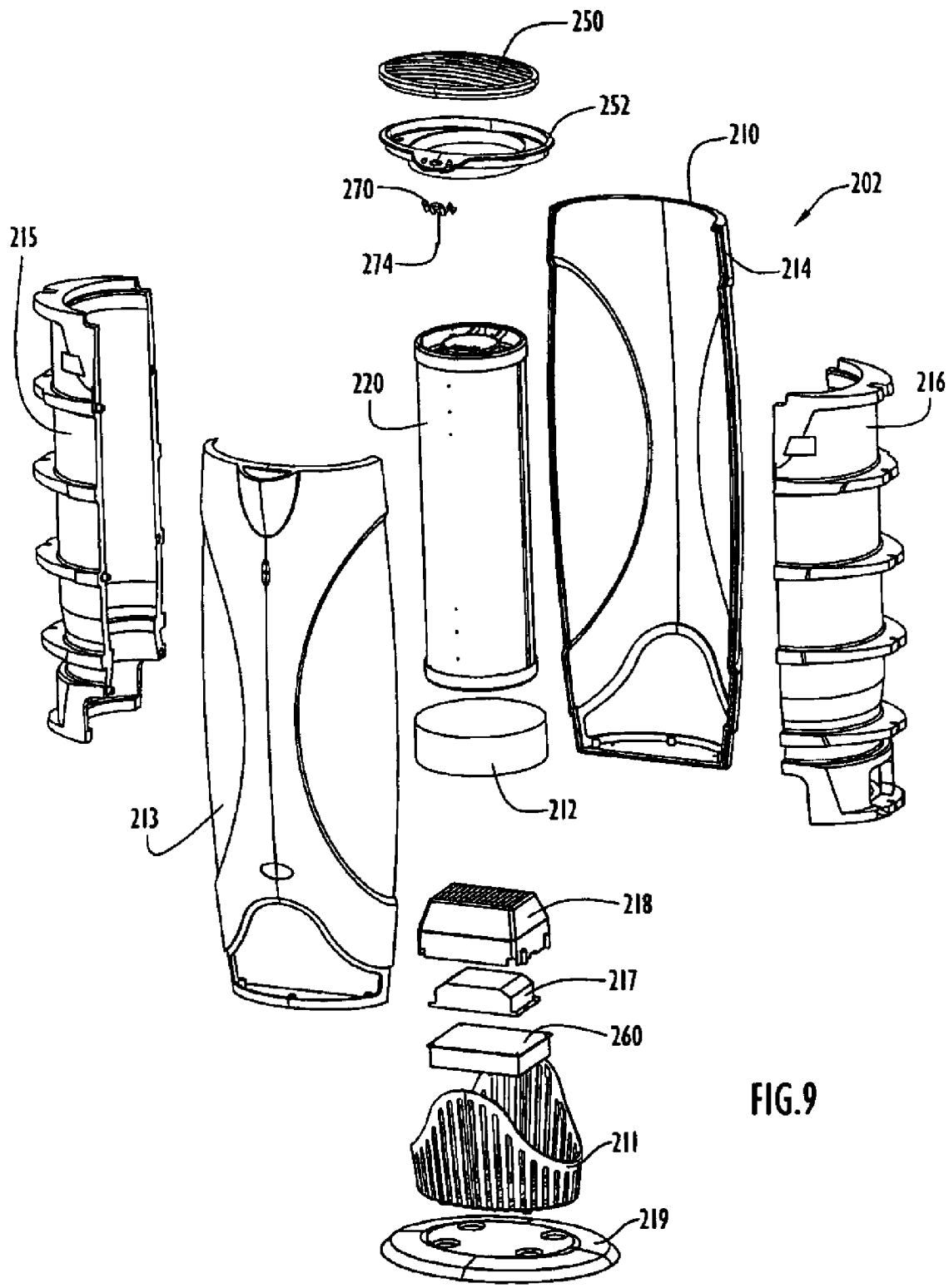
FIG. 9 is an exploded view in perspective of an alternative embodiment of an air purification system in accordance with the present invention.
Figure 10:
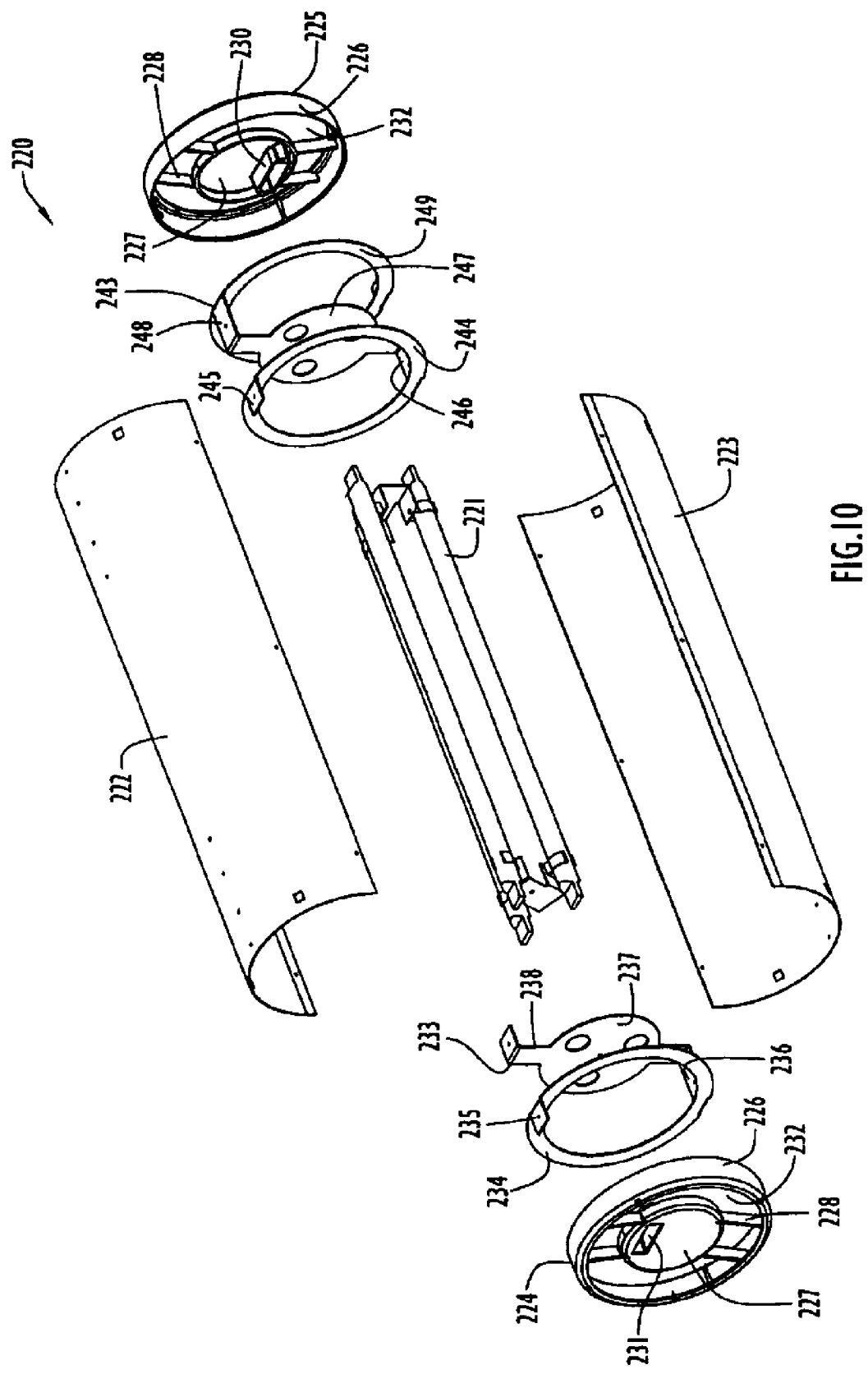
FIG. 10 is an exploded view in perspective of the cartridge of the system of FIG. 9.

An alternative embodiment of a system is depicted in FIGS. 9 and 10. This system is similar to the system described above, with the exception that the bulbs are supported at both the upstream and downstream ends of the cartridge with a baffle plate configuration as described below. System 202 includes an elongated housing 210 that is similar in configuration to the housing 10 including an internally mounted chassis 215, 216 containing a replaceable cartridge 220 in which one or more ultraviolet radiation bulbs 221 are mounted. The bulbs are elongated cylindrical UV bulbs oriented longitudinally within the cartridge in a similar manner as described above for the system of FIGS. 1–8, where the axes of the bulbs are oriented parallel to the direction of net air flow through the housing. An intake grill 211 and fan 212 are disposed at the inlet or upstream end of the housing, although the fan may be located at the outlet or downstream end to draw, rather than push, air through the housing.

The housing 210 is preferably constructed of injection molded plastic including two substantially symmetrical halves 213, 214 externally contoured to provide an attractive appearance as in the system described above. Alternatively, the housing may be constructed of any suitable metals (e.g., aluminum, galvanized and/or stainless steel) or other suitable rigid covering. Likewise, the hollow chassis is typically constructed of foam or molded plastic including two substantially symmetrical halves 215, 216, each with outwardly projecting ribs contacting the interior surface of the housing to serve as support spacers for positioning the chassis substantially centered interiorly of the housing, preferably in coaxial orientation with the housing.

The cartridge 220 is preferably in the form of a UV-opaque cylinder removably mounted in coaxial orientation within the chassis. In the embodiment of FIGS. 9 and 10, the cartridge is made of two substantially similar semi-cylindrical half shell sections 222, 223 of aluminum (or any other suitable reflective material, including, e.g., plastic with a reflective metal coating) so as to provide reflective surface portions within the UV chamber, and three parallel-mounted UV sources or bulbs are mounted in the cartridge. The germicidal UV radiation sources generate radiation having a wavelength of approximately 254 nanometers (the wavelength known to inactivate the DNA/RNA of and/or to destroy bacteria, viruses, mold spores and the like). The bulbs are powered by an electronic AC ballast 217 (for use in stationary operation), or an electronic DC ballast connected to a battery to enable the system to be portable and used in mobile environments (e.g., cars, boats, trucks, trailers, etc.).

An electronics housing 218, secured to the housing base 219, contains the system electrical and electronics components including a processor, a power supply, and related electronic circuitry (indicated generally as element 260 in FIG. 9). The circuitry controls on-off operation of the fan and the UV sources and may also control appropriate indicators such as lamps, LCD and/or LED displays, etc., that provide information regarding the operating status of the unit (e.g., similar to the system described above). The cartridge 220 is adapted to be periodically replaced, thereby facilitating versatility and easy maintenance of the system.

The base 219 serves as a stand that permits the unit to be positioned anywhere on a floor in a room. Alternatively, the unit may be configured for mounting on or installation within a wall or ceiling.

The ends of the cartridge 220 have respective substantially identical end caps 224, 225 mounted thereon. Each end cap is in the form of an outer ring or annulus 226 with support struts 228 extending inwardly to retain a central generally circular bulb-mounting plate 227. The outer ring has a short axial length with an inside diameter substantially equal to the outside diameter of the cartridge wall. In this way the outer ring fits closely over the end of the cartridge to which it is secured by pop rivets, or the like. In the outlet end cap 225 the central mounting plate supports a plug or receptacle connector 230 for receiving AC power applied to the unit. In the inlet end cap 224 the connector location is left open, forming a small opening 231 in the plate and thereby providing a flow restriction for air flow into the cartridge. Additional air flows around the central mounting plate periphery through the generally annular space 232 provided between the mounting plate and the outer ring. That annular flow path is interrupted by the support struts 228 supporting the central mounting plate 227.

An intake baffle unit 233 includes an annular baffle member 234 having an outside diameter substantially equal to the inside diameter of the outer ring of the inlet end cap 224. The inside diameter of the annular baffle member is considerably smaller and defines a radial thickness dimension extending into the path of air flow through the cartridge. A first axially-oriented support tab 235 is secured to the annular baffle member 234 and extends a short distance upstream to a location in contact with the interior surface of the cartridge shell 222. Support tab 235 is secured to the cartridge shell 222 by means of a pop rivet, or the like, to fix the inlet baffle unit 233 in place relative to the cartridge wall. A second axially-oriented support tab 236 extends downstream from annular baffle member 234 at a location spaced approximately 180° from the first support tab 235. Support tab 236 includes a radially inward terminus segment that supports a generally circular bulb mounting plate 237 inside the cartridge in a plane perpendicular to the longitudinal axis of cartridge 220 and centered on that axis. Support tab 236 is adapted to be secured to cartridge shell 223 by a pop rivet, or the like. A mounting tab 238 extends radially outward from mounting plate 237 at an edge location spaced 180° from the terminus of support tab 236. Mounting tab 238 is adapted to be secured to the cartridge shell 222 by means of a pop rivet, or the like. There are three mounting apertures defined through plate 237 at 120°-spaced locations equidistant from the center of the plate. Each mounting aperture in plate 237 is configured to receive and support an upstream end of a respective UV bulb of the lamp assembly 221.

An outlet baffle unit 243 includes an annular baffle member 244 having an outside diameter substantially equal to the inside diameter of the cartridge 220. The inside diameter of annular baffle member 244 is considerably smaller and defines a radial thickness dimension projecting into the path of air flow through the cartridge. A first axially-oriented support tab 245 is secured to annular baffle member 244 and extends a short distance upstream to a location in contact with the interior surface of cartridge shell 222. Support tab 245 is secured to cartridge shell 222 by means of a pop rivet, or the like, to fix the inlet baffle unit 233 in place relative to the cartridge wall. A second axially-oriented support tab 246 extends downstream from annular baffle member 244 at a location spaced approximately 180° from the first support tab 245. Support tab 246 includes a radially inward terminus segment that supports a generally circular bulb mounting plate 247 inside the cartridge in a plane perpendicular to the longitudinal axis of cartridge 220 and centered on that axis. Support tab 246 is adapted to be secured to cartridge shell 223 by a pop rivet, or the like. A mounting tab 248 extends radially outward from mounting plate 247 at an edge location spaced 180° from the terminus of support tab 246. Mounting tab 248 is adapted to be secured to the cartridge shell 222 by means of a pop rivet, or the like. There are three mounting apertures defined through plate 247 at 120°-spaced locations equidistant from the center of the plate. Each mounting aperture in plate 247 is configured to receive and support a downstream end of a respective UV bulb of the lamp assembly 221. A further baffle member 249 is secured at its outermost edge to the downstream terminus of tab 248. Baffle member 249 has an outside diameter substantially equal to the inside diameter of cartridge 220 and an inside diameter which is considerably smaller and defines a radial thickness dimension extending into the path of air flow through the cartridge.

The UV emissions from the lamp assembly 221 are blocked from escaping from the unit and causing damage to persons and animals viewing the unit. At the upstream end, this blocking function is achieved by the positioning of the fan 212, electronics housing 218 and intake grill 211. At the downstream end, light blocking is effected by appropriate screening and ceramic lamp bases (not shown) in combination with an outlet grill 250 and bezel 252 secured to the housing 210 and chassis 215, 216, respectively.

The system 202 further includes a button tree 270, an LED indicator 274, a processor and control circuitry similar to that described above for the system of FIGS. 1–8. Optionally, the system 202 may further include a filter and/or photocatalyst similar to those described above and positioned in similar locations as the previous system. Thus, the processor of system 202 controls system operations in a manner similar to the previously described system.

The flow of air through the cartridge 220 of system 200 is described as follows. In operation, air is caused to flow into and through the unit by fan 212. The incoming air is directed into the cartridge and is initially redirected and perturbed by struts 228 and plate 227 in end cap 224. In particular, the initially cylindrical and potentially laminar air stream is compressed from its interior outward into an annular stream in order to flow past plate 227. The portions of that stream flowing past the circumferential edge of plate 227 and past the struts 238 create vortical or eddy components that introduce turbulence into the overall flow. A small portion of the air flows through aperture 231 in plate 227. The flow net cross-sectional area through end cap 224 is smaller than the flow cross-section immediately upstream of the end cap, so that there is a net flow restriction and reduction in flow rate. The outer edge of the stream is then forced inward into a more cylindrical (rather than annular) stream configuration by baffle member 234, the inner annular edge of which induces additional vortices that increase turbulence in the flow. Closely downstream of baffle member 234 the flow is caused to resume an annular cross-section in order to flow past plate 237. The result is a further restriction and slow down as well as the introduction of more turbulence in the air flowing toward and then along the lamp assembly 221. In a similar manner, the flow is restricted and slowed, and turbulence is induced therein, by the outlet baffle members 244 and 249 and the interposed plate 247. Although not described in detail, the end caps are provided with metal or plastic safety grids to prevent injury to individuals who might otherwise insert fingers into the unit.

The flow past the lamp assembly is cylindrically contained by the radial proximity to the lamp assembly of the surrounding walls defined by the cartridge shells 222, 223. Accordingly, the flowing air stream in the cartridge is constantly mixed by the turbulence introduced in the manner described such that substantially all of the turbulent air comes into direct contact with one or more bulb surfaces at one time or other. This, combined with the increase in residence time of air in the cartridge, resulting from the slow down of flow caused by the flow restrictions, optimizes the flow parameters to maximize the germicidal treatment of the air by the UV radiation from lamp assembly 221.

The primary goal of the present invention is to optimize the exposure of the air flowing through the system to the germicidal UV radiation in order to maximize the kill rate of bacteria, viruses, spores, etc., in air. This is achieved through the optimization of a number of system parameters including, without limitation: the UV chamber dimensions (i.e., the internal dimensions of the cartridge), the size, number and intensity of UV bulbs provided within the UV chamber, the placement and location of UV bulbs within the chamber to ensure adequate UV radiation exposure to plugs of air flowing through the UV chamber, fan size and operability to deliver air flow at a sufficient capacity through the UV chamber, the use and degree of curvature of reflective surfaces within the UV chamber, the degree of baffling provided at the upstream end, downstream end and/or at other locations within the housing to effect a sufficient degree of turbulent mixing of the air flow within the UV chamber, and controlling the residence time of air flowing through the UV chamber by sufficiently restricting air flow at the upstream end, downstream end and/or at other locations within the housing.

The systems described above achieve the desired kill rate of bacteria, viruses, spores, etc., in air by providing suitable baffling at upstream and downstream locations within the housing. In particular, the systems described above include baffling disposed upstream and downstream of the UV bulbs, so as to effectively induce turbulent mixing to the air stream flowing through the UV chamber while facilitating a simple design that permits easy installation and removal of bulbs from the chamber. The systems further provide adequate flow restriction to increase residence time within the housing to ensure a sufficient kill rate is achieved. Further, the bulb spacing and orientation in the UV chamber, the number of UV bulbs utilized, the dimensions of the UV chamber, and the placement of a filter are selected to optimize exposure of the air flow to UV radiation and thus the kill/removal rate of contaminants within the air. Further, the combined baffle design of the outlet grill and the cartridge end cap substantially limit or prevent UV radiation from escaping the housing during system operation. The use of a curved, reflective surface within the UV chamber also enhances UV intensity and kill rate.

Exemplary dimensions for bulbs that may be utilized in the three bulb lamp assembly described above for the previous systems are between about 12–16 inches (about 30.5–40.6 cm) in length and about 0.6 inch (about 1.5 cm) in diameter, with each bulb drawing about 425 mA at an AC line voltage of 120V. The three bulbs can be oriented to fit within a circle having a diameter of about 2.11 inches (about 5.36 cm). The UV chamber, which is the interior or hollow space defined within the cartridge, is preferably about 5.46 inches (about 13.9 cm) in diameter and of sufficient length to contain the UV bulbs. The cartridge is designed with suitable dimensions to define such a UV chamber, and preferably includes a reflective internal surface that is rounded (e.g., cylindrical) to intensify the UV radiation within the UV chamber. Thus, the combination of at least the UV bulb design and orientation within the UV chamber, the size of the UV chamber, and the baffle structure within the housing ensure turbulent air flow through the UV chamber as well as close contact between the UV bulbs and air flowing through the UV chamber. This in turn maximizes the kill rate of contaminants entrained in the air stream.

Although a three bulb lamp assembly is shown in the preferred embodiment, it is to be understood that the kill rate can be adjusted upward or downward by using more or fewer bulbs or lamps with higher or lower output radiation. In addition, elongated UV bulbs are preferred and are considered to be more efficient than spot or other bulb configurations since the exposure time of air in the UV chamber is maximized for long bulb configurations. The bulbs can be mounted in any suitable manner within the UV chamber, with one or both ends of the bulbs mounted in mounting plates secured against the UV chamber walls and/or secured to the end caps or other end wall supporting structure within the UV chamber.

The cartridges described above may be of any shape or size, and may include any quantity of UV chambers, radiation sources or other system electrical or other components. The radiation sources may be implemented by combination bulbs or independent radiation sources emitting radiation at particular wavelengths. The cartridges can be disposable and periodically replaced. However, a base and cartridge may be implemented as an integral disposable unit. In addition, while the preferred embodiment of the invention provides the UV chamber in the form of a replaceable cartridge, it must be understood that a UV permanent chamber may be provided within the scope of the invention. In other words, other embodiments encompassed under the present invention can have UV chambers that are permanently disposed within and not removable from the housing.

The base may be of any shape or size and may include any suitable number and types of mounting elements to secure the system to a support structure. The housing may include any quantity (e.g., at least one) of ballasts, fans or other electrical or system components arranged in any fashion, and may be constructed of any suitable materials.

Any suitable number and types of baffles having any suitable configurations may be provided at or near the upstream and downstream ends of the system housing to provide a sufficient restriction and mixing of air flow currents so as to generate a selected level of turbulence in the air stream. In addition, baffles may be provided at any suitable locations within the UV chamber to further enhance the turbulent air flow and resultant kill rate of contaminants within the air stream. The downstream end of the system may include any suitable fin or baffle configuration that increases residence time of air flow within the system while substantially limiting or preventing the escape of UV radiation from the UV chamber of the system housing.

The combination of UV chamber with baffle structure can be implemented in a stand-alone structure, such as the systems described above or, alternatively, integrated in an existing structure including, without limitation, wall and ceiling units, air treatment systems, such as HVAC systems, humidifiers, air conditioning and/or heating systems, and/or other devices to purify air streams within those devices and return purified air to the surrounding environment. The systems may be disposed at any locations within the devices prior, subsequent or during treatment of the air by those devices for purifying an air stream.

The bulb end-caps may include any configuration or conventional guiding mechanisms to align the end-cap for power or other connections. The power plugs may be of any shape or size, may be implemented by any conventional or other connector, and may include any quantity (e.g., at least one) of receptacles for connecting corresponding pins to a power source. Similarly, the female plug may be implemented by any conventional or other plug, and may include any quantity (e.g., at least one) of extensions or pegs or other configurations to align the end-cap with the power plug. Further, the end-cap may include any quantity (e.g., at least one) of pins of any shape or size and arranged in any fashion to establish power connections for the radiation source.

The cartridge may be constructed of any suitable materials and have any suitable dimensions and geometric configuration to provide a UV chamber of sufficient dimensions to suitably house the UV source. The cartridge may include reflective surfaces at any suitable locations within the UV chamber.

The end caps of the cartridge may include slots, windows or other openings of any quantity (e.g., at least one), shape or size, arranged in any fashion on the end cap. Any suitable number of electrical connectors of any suitable type may be provided on one or both end caps to facilitate releasable connection between the UV source disposed within the cartridge and the ballast providing power to the UV source. Any suitable handle or other gripping device may be provided on the end caps to allow easy removal of the cartridge by a user.

Any suitable number of fluid flow controllers (e.g., fans, blowers, pumps, etc.) may be provided at any suitable locations within the system to push or draw air in any one or more selected directions through the UV chamber for processing by the UV source. The fluid flow controllers can be adjustable to any selected number of speed control settings.

Any suitable number of input control devices (e.g., buttons) may be provided to control system power, the operation of the fluid flow controllers and/or other system functions. In addition, any suitable number and type of display indicators (e.g., LED and/or LCD indicators, audio indicators, etc.) may be provided to provide the user with information relating to various conditions during system operation.

The system may utilize any suitable processor or controller in combination with any other suitable electronic circuit components to facilitate operation of the system in the manner described above. Any suitable number of electronic ballasts of any suitable type may be utilized to provide power to the UV source, and any suitable number of safety and/or interlock switches can be provided at any one or more suitable locations to disable power to the UV source when one or more system components are removed from the system.

It is to be understood that the terms "top", "bottom", "upper", "lower", "up", "down", "height", "width", "length", "thickness", "depth", "front" and "rear" are used herein merely to facilitate descriptions of points of reference and do not limit the present invention to any specific configuration or orientation.

Having described novel systems and corresponding methods for removing contaminants from gaseous fluids, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A system for purifying a gaseous fluid comprising:
   a housing including an inlet and an outlet;
   a hollow cartridge disposed within and removable from the housing, the hollow cartridge including an elongated UV chamber disposed within the hollow cartridge;
   a UV radiation source disposed longitudinally within the UV chamber of the hollow cartridge;
   at least one baffle structure disposed at an upstream location within the housing to restrict flow as well as to generate a turbulent flow of the gaseous fluid within the UV chamber; and
   a fan disposed at a selected location within the housing to facilitate a flow of the gaseous fluid through the housing at a selected flow rate;
   wherein the dimensions of the UV chamber and UV source and the configuration of the baffle structure are selected to increase the exposure time and mixing of fluid flowing through the UV chamber as well as increase the proximity of the flowing fluid to the UV source.

2. The system of claim 1, wherein the baffle structure is disposed at a location within the housing that is upstream from the UV source.

3. The system of claim 2, wherein the UV source comprises a plurality of elongated UV bulbs oriented in a selected configuration within the UV chamber to provide a flow path for the fluid between the UV bulbs and internal wall surface portions of the UV chamber as well as at least one flow path between adjacent bulbs.

4. The system of claim 3, wherein the UV source includes three elongated UV bulbs arranged at 120° spaced locations from a central axis defined between and extending parallel to the UV bulbs.

5. The system of claim 2, wherein the baffle structure includes a mounting member disposed near an upstream end of the cartridge, the mounting member securing an upstream end of the UV source within the cartridge.

6. The system of claim 2, wherein the cartridge includes an end cap disposed at a downstream end of the cartridge, and the end cap includes a support structure that supports a downstream end of the UV source within the cartridge.

7. The system of claim 6, wherein the cartridge further includes a handle secured to the end cap to facilitate removal of the cartridge from the housing.

8. The system of claim 6, wherein the cartridge further includes an electrical receptacle secured to the end cap and in electrical contact with the UV source, and the electrical receptacle is configured to releasably engage with an electrical supply source.

9. The system of claim 6, wherein the fan is adjustable to different operating speeds, and the system further comprises:
   at least one input button to facilitate selective control by a user of the operating speed of the fan; and
   a processor in communication with at least the input button and the fan to control the operating speed of the fan based upon input signals provided by the input button.

10. The system of claim 9, further comprising:
    an indicator device controlled by the processor to provide at least one of visual indications and audio indications to the user during system operation.

11. The system of claim 10, wherein the indicator device includes a tri-color LED display.

12. The system of claim 10, wherein the processor controls the indicator device to provide an indication to the user of at least one of the following conditions: the UV source is operating within a selected percentage of an anticipated life expectancy of the UV source, the UV source is approaching the anticipated life expectancy, and the UV source has exceeded the anticipated life expectancy.

13. The system of claim 6, further comprising:
    an outlet grill removably secured at a downstream end of the housing, wherein the outlet grill is removed from the housing to facilitate removal of the cartridge.

14. The system of claim 13, further comprising:
    an electrical switch disposed at the downstream end of the housing and releasably engageable with the outlet grill, wherein the electrical switch is opened when the outlet grill is removed from the housing to prevent operation of the UV source.

15. The system of claim 13, wherein at least one of the outlet grill and the end cap includes a second baffle structure to prevent a selected amount of UV light from escaping the housing and to provide a winding flow path for fluid flowing at the downstream end of the housing during system operation.

16. The system of claim 15, wherein the second baffle structure comprises a first set and a second set of frusto-conical baffles, the first set is disposed in the end cap and defines a series of openings extending through the end cap and between the baffles, and the second set is disposed in the outlet grill and defines a series of openings extending through the outlet grill and between the baffles.

17. The system of claim 16, wherein, upon assembly of the cartridge and the outlet grill with respect to the housing, the frusto-conical baffles of the first and second sets are oriented such that the diameter of each baffle in the first set increases in an upstream direction of the system and the diameter of each baffle in the second set increases in a downstream direction of the system.

18. The system of claim 2, further comprising a second baffle structure disposed at a downstream location within the housing, wherein the second baffle structure is configured to restrict the flow of fluid from the outlet of the housing as well as to block a selected amount of UV light from escaping the housing during system operation.

19. The system of claim 1, further comprising:
    a filter disposed between the UV source and the outlet of the housing.

20. A method of enhancing purification of a gaseous fluid utilizing a system including a housing, a removable hollow cartridge disposed within the housing and including an elongated UV chamber disposed within the hollow cartridge, a UV radiation source disposed longitudinally within the UV chamber of the hollow cartridge, at least one baffle structure disposed at an upstream location within the housing, and a fan, the method comprising the steps of:
    providing electrical power to the UV radiation source to facilitate generation of UV radiation within the UV chamber;
    flowing fluid through the housing and the UV chamber via the fan;
    facilitating the generation of turbulence and mixing of fluid flowing into the UV chamber via the baffle structure;

restricting fluid flow through the UV chamber to increase exposure time of the fluid to the UV radiation; and removing the cartridge from the housing to facilitate at least one of providing a new cartridge within the housing and replacing the UV source within the cartridge.

21. The method of claim 20, wherein the baffle structure is disposed at a location within the housing that is upstream from the UV source.

22. The method of claim 20, wherein the UV source comprises a plurality of elongated UV bulbs oriented in a selected configuration within the UV chamber to provide an a flow path for the fluid between the UV bulbs and internal wall surface portions of the UV chamber as well as at least one flow path between adjacent bulbs.

23. The method of claim 22, wherein the UV source includes three elongated UV bulbs arranged at 120° spaced locations from a central axis defined between and extending parallel to the UV bulbs.

24. The method of claim 20, wherein the baffle structure includes a mounting member disposed near an upstream end of the cartridge, the mounting member securing an upstream end of the UV source within the cartridge.

25. The method of claim 20, wherein the cartridge includes an end cap disposed at a downstream end of the cartridge, and the end cap includes support structure that supports a downstream end of the UV source within the cartridge.

26. The method of claim 25, wherein the cartridge further includes a handle secured to the end cap to facilitate removal of the cartridge from the housing.

27. The method of claim 25, wherein the cartridge further includes an electrical receptacle secured to the end cap that is in electrical contact with the UV source and in releasable electrical contact with an electrical supply source, and the electrical receptacle is disengaged with the electrical supply source prior to removal of the cartridge from the housing.

28. The method of claim 25, wherein the fan is adjustable to different operating speeds, the system further includes at least one input button and a processor in communication with the input button and the fan, and the method further comprises:

facilitating selective control of the operating speed of the fan, via the processor, by pressing the at least one input button.

29. The method of claim 28, wherein the system further includes an indicator device in communication with the processor, and the method further comprises:

providing at least one of a visual indication and an audio indication to the user, via control of the indicator device by the processor, during system operation.

30. The method of claim 29, wherein the indicator device includes a tri-color LED display, and the processor controls the LED display to provide a plurality of different indications to the user during system operation.

31. The method of claim 30, the processor controls the LED display to provide an indication to the user of at least one of the following conditions: the UV source is operating within a selected percentage of an anticipated life expectancy of the UV source, the UV source is approaching the anticipated life expectancy, and the UV source has exceeded the anticipated life expectancy.

32. The method of claim 25, wherein the system further includes an outlet grill removably secured at a downstream end of the housing, and the method further comprises:

removing the outlet grill from the housing prior to removal of the cartridge.

33. The method of claim 32, the system further includes an electrical switch disposed at the downstream end of the housing and releasably engageable with the outlet grill, and the method further comprises:

facilitating the opening of the electrical switch when the outlet grill is removed from the housing to prevent operation of the UV source.

34. The method of claim 32, wherein at least one of the outlet grill and the end cap includes a second baffle structure, and the method further comprises:

preventing a selected amount of UV light from escaping the housing and providing a winding flow path for fluid flowing at the downstream end of the housing via the second baffle structure.

35. The method of claim 34, wherein the second baffle structure comprises a first set and a second set of frusto-conical baffles, the first set is disposed in the end cap and defines a series of openings extending through the end cap and between the baffles, and the second set is disposed in the outlet grill and defines a series of openings extending through the outlet grill and between the baffles.

36. The method of claim 35, wherein, upon assembly of the cartridge and the outlet grill with respect to the housing, the frusto-conical baffles of the first and second sets are oriented such that the diameter of each baffle in the first set increases in an upstream direction of the system and the diameter of each baffle in the second set increases in a downstream direction of the system.

37. The method of claim 21, wherein the system further includes a second baffle structure disposed at a downstream location within the housing, and the method further comprises:

preventing a selected amount of UV light from escaping the housing and providing a winding flow path for fluid flowing at the downstream end of the housing via the second baffle structure.

38. The method of claim 20, wherein the system further includes a filter disposed between the UV source and an outlet of the housing, and the method further comprises:

filtering fluid flowing through the housing.

39. A system for purifying a gaseous fluid comprising:

a means for housing an elongated UV chamber;

a means for generating UV radiation disposed longitudinally within the UV chamber;

a means for selectively removing the elongated UV chamber including the means for generating UV radiation from the means for housing the elongated UV chamber;

a means for restricting flow as well as generating a turbulent flow of the gaseous fluid within the UV chamber, the means for restricting being disposed at an upstream location within the means for housing; and a means for generating a flow of the gaseous fluid through the means for housing;

wherein the dimensions of the UV chamber and the means for generating UV radiation and the means for restricting flow are selected to increase the exposure time and mixing of fluid flowing through the UV chamber as well as increase the proximity of the flowing fluid to the UV source.

40. A system for purifying a gaseous fluid comprising:

a housing including an inlet, an outlet, and an elongated UV chamber disposed within the housing;

a UV radiation source disposed longitudinally within the UV chamber;

a filter disposed between the UV source and the outlet of the housing;

at least one baffle structure disposed at an upstream location within the housing to restrict flow as well as to generate a turbulent flow of the gaseous fluid within the UV chamber; and a fan disposed at a selected location within the housing to facilitate a flow of the gaseous fluid through the housing at a selected flow rate;

wherein the dimensions of the UV chamber and UV source and the configuration of the baffle structure are selected to increase the exposure time and mixing of fluid flowing through the UV chamber as well as increase the proximity of the flowing fluid to the UV source.

41. A system for purifying a gaseous fluid comprising:

a housing including an inlet, an outlet, and an elongated UV chamber disposed within the housing;

a UV radiation source disposed longitudinally within the UV chamber, the UV source comprising three elongated UV bulbs arranged at 120° spaced locations from a central axis defined between and extending parallel to the UV bulbs;

at least one baffle structure disposed at an upstream location within the housing to restrict flow as well as to generate a turbulent flow of the gaseous fluid within the UV chamber; and a fan disposed at a selected location within the housing to facilitate a flow of the gaseous fluid through the housing at a selected flow rate;

wherein the dimensions of the UV chamber and UV source and the configuration of the baffle structure are selected to increase the exposure time and mixing of fluid flowing through the UV chamber as well as increase the proximity of the flowing fluid to the UV source.

42. A method of enhancing purification of a gaseous fluid utilizing a system including a housing with an elongated UV chamber disposed therein, a UV radiation source disposed longitudinally within the UV chamber, at least one baffle structure disposed at an upstream location within the housing, a filter disposed between the UV source and an outlet of the housing, and a fan, the method comprising the steps of:

providing electrical power to the UV radiation source to facilitate generation of UV radiation within the UV chamber;

flowing fluid through the housing and the UV chamber via the fan;

facilitating the generation of turbulence and mixing of fluid flowing into the UV chamber via the baffle structure;

restricting fluid flow through the UV chamber to increase exposure time of the fluid to the UV radiation; and filtering fluid flowing through the housing.

43. A method of enhancing purification of a gaseous fluid utilizing a system including a housing with an elongated UV chamber disposed therein, a UV radiation source disposed longitudinally within the UV chamber, the UV source including three elongated UV bulbs arranged at 120° spaced locations from a central axis defined between and extending parallel to the UV bulbs, at least one baffle structure disposed at an upstream location within the housing, and a fan, the method comprising the steps of:

providing electrical power to the UV radiation source to facilitate generation of UV radiation within the UV chamber;

flowing fluid through the housing, through the UV chamber and around the UV bulbs via the fan;

facilitating the generation of turbulence and mixing of fluid flowing into the UV chamber via the baffle structure; and restricting fluid flow through the UV chamber to increase exposure time of the fluid to the UV radiation.

* * * * *